(12) United States Patent
Rappuoli et al.

(10) Patent No.: US 7,867,498 B2
(45) Date of Patent: *Jan. 11, 2011

(54) POLYPEPTIDE CARRIER PROTEIN

(75) Inventors: Rino Rappuoli, Castelnuovo Berardenga (IT); Guido Grandi, Segrate (IT)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/383,545

(22) Filed: Mar. 25, 2009

(65) Prior Publication Data

US 2009/0227770 A1 Sep. 10, 2009

Related U.S. Application Data

(60) Division of application No. 11/030,635, filed on Jan. 6, 2005, now Pat. No. 7,538,207, which is a continuation of application No. 09/674,183, filed as application No. PCT/IB99/00844 on Apr. 27, 1999, now Pat. No. 6,855,321.

(30) Foreign Application Priority Data

Apr. 27, 1998 (GB) .................................. 0908932.9

(51) Int. Cl.
| | |
|---|---|
| A61K 39/00 | (2006.01) |
| A61K 39/38 | (2006.01) |
| A61K 39/295 | (2006.01) |
| A61K 39/116 | (2006.01) |
| A61K 39/08 | (2006.01) |
| A61K 39/10 | (2006.01) |
| A61K 39/095 | (2006.01) |
| A61K 38/00 | (2006.01) |
| A61K 39/015 | (2006.01) |
| A61K 39/29 | (2006.01) |
| A61K 45/00 | (2006.01) |
| C07K 14/00 | (2006.01) |

(52) U.S. Cl. ............... 424/192.1; 424/234.1; 424/201.1; 424/203.1; 424/185.1; 424/282.1; 424/247.1; 424/240.1; 424/268.1; 424/210.1; 424/227.1; 424/250.1; 424/239.1; 424/832; 424/184.1; 514/2; 530/350; 530/300; 530/825; 530/822; 530/826; 530/806; 530/807

(58) Field of Classification Search .................. None
See application file for complete search history.

(56) References Cited

U.S. PATENT DOCUMENTS

| | | | |
|---|---|---|---|
| 4,695,624 | A | 9/1987 | Marburg et al. |
| 4,870,009 | A | 9/1989 | Evans et al. |
| 4,882,317 | A | 11/1989 | Marburg et al. |
| 4,902,506 | A | 2/1990 | Anderson et al. |
| 5,651,971 | A | 7/1997 | Lees |
| 5,728,385 | A | 3/1998 | Classen |
| 6,855,321 | B1 * | 2/2005 | Rappuoli et al. ......... 424/192.1 |
| 2008/0260769 | A1 | 10/2008 | Capecchi et al. | |

FOREIGN PATENT DOCUMENTS

| | | |
|---|---|---|
| EP | 0270295 A2 | 6/1988 |
| EP | 0429816 A | 6/1991 |
| WO | WO 86/05790 | 9/1986 |
| WO | WO 92/21374 | 10/1992 |
| WO | WO 96/03144 | 7/1995 |
| WO | WO 98/43677 | 8/1998 |
| WO | 2006/011060 A2 | 2/2006 |

OTHER PUBLICATIONS

Agadjanyan, et al., "Peptide mimicry of carbohydrate epitopes on human immunodeficiency virus," *Nature Biotechnol* 15:547-551 (1997).

Ahlers, et al., "Construction of an hiv-1 peptide vaccine containing a multideterminant helper peptide linked to a V3 loop peptide 18 inducing strong neutralizing antibody responses in mice of multiple MHC haplotypes after two immunizations," *J Immunol* 150(12):5647-5665 (1993).

An, et al., "A multivalent minigen vaccine, containing B-cell, cytotoxic T-lymphocyte and Th epitopes from several microbes, induces appropriate responses in vivo and confers protection against more than one pathogen," *J Virol* 71(3):2292-2302 (1997).

Andreoni, et al., "Vaccination and the role of capsular polysaccharide antibody in prevention of recurrent meningococcal disease in late complement component-deficient individuals," *J Infect Dis* 168:227-231 (1993).

Anderson, et al., "Antibody responses to *Haemophilus influenza* type b and diphtheria toxin induced by conjugates of oligosaccharides of the type b capsule with the nontoxic protein CRM," *Infect Immun* 39(1):233-238 (1983).

Anderson, et al., "Immunization of 2-month-old infants with protein-coupled oligosaccharides derived from the capsule of *Haemophilus influenza* type b," *J Pediatrics* 107:346-351 (1985).

Anderson, et al., "Immunogens consisting of oligosaccharides from the capsule of *Haemophilus influenza* type b coupled to diphtheria toxoid or the toxin protein CRM197," *J Clin Invest* 76:52-29 (1985).

Bixler, et al., "Synthetic peptide representing a T-cell epitope of CRM197 substitutes as carrier molecule in a Haemophilus influenza type b (HIB) conjugate vaccine," *Adv Exper Med Bio* 251:175-180 (1989).

Chang, et. al., "Anergy in immature b lymphocytes differntial responses to receptor-mediated stimulation and T helper cells," *J Immun* 147(3):750-756 (1991).

(Continued)

Primary Examiner—S. Devi
(74) Attorney, Agent, or Firm—Helen Lee; Otis Littlefield; Roberta Robins

(57) ABSTRACT

The invention relates to polypeptide carrier proteins that comprise at least five CD4+ T cell epitopes, for conjugation to capsular polysaccharides. The carrier proteins are useful as components of vaccines that can elicit a T-cell dependent immune response. These vaccines are particularly useful to confer protection against infection from encapsulated bacteria in infants between the ages of 3 months and about 2 years.

8 Claims, 14 Drawing Sheets

OTHER PUBLICATIONS

Christodoulides, et al., "Immunization with a multiple antigen peptide containing defined B- and T-cell epitopes: production of bacteriocidal antibodies against group B neisseria meningitides," *Microbiology* 140(11):2951-2960 (1994).

Constantino, et al., "Development and phase 1 clinical testing of a conjugate vaccine against meningococcus A and C," *Vaccine* 10(10):691-698 (1992).

De Velasco, et al., "Synthetic peptides representing T-cell epitopes act as carriers in pneumococcal polysaccharide conjugate vaccines," *Inf Immun* 63(3):961-968 (1995).

Dick, et al., "Glycoconjugates of bacterial carbohydrate antigens," *Conjugate vaccines* 10:48-114 (1989).

Etlinger, et al., "Use of prior vaccinations for the development of new vaccines," *Science* 249:423-425 (1990).

Falugi, et al., "Rationally designed strings of promiscuous CD4(+) T cell epitopes provide help to Haemophilus influenzae type b oligosaccharide: a model for new conjugate vaccines," *Eur J Immunol* 31:3816-3824 (2001).

Goldblatt, et al., "Role of cell wall polysaccharide in the assessment of IgG antibodies to the capsular polysaccharides of streptococcus pneumoniae in childhood," *J Inf Dis* 166:632-634 (1992).

Good, et al., "Construction of synthetic immunogen: use of new T-helper epitope on malaria circumsporozite protein," *Science* 235:1059-1062 (1987).

Grandoff, et al., "Effect of immunity to the carrier protein on antibody responses to *Haemophilus influenza* type b conjugate vaccines," *Vaccine* 11(1):546-551 (1993).

Grandoff, et al., "Introduction of immunologic memory in infants primed with *Haemophilus influenza* type b conjugate vaccines," *J Infect Dis* 168:663-671 (1993).

Hayward, et al., "Induction of plasma cell differentiation of human fetal lymphocytes: evidence for functional immaturity of t and b cells," *J Immun* 119(4):1213-1217 (1977).

Holmes, et al., "The biology of *Haemophilus influenza* type b vaccination failure," *J Infect Dis* 165:5121-5128 (1992).

Insel, et al., "Oligosaccharide-protein conjugate vaccines induce and prime for oligoclonal IgC antibody responses to the *Haemophilus influenza* b capsular polysaccharide in human infants," *J Exp Med* 163:262-269 (1986).

Ishioka, et al., "MHC interaction and T cell recognition of carbohydrates and glycopeptides," *J Immun* 148:2446-2451 (1992).

Houdebine, "Transgenic animal bioreactors," *Transgenic Research* 9:305-320 (2000).

Jennings, et al., "Immunochemistry of groups A, B, and C meningococcal polysaccharide-tetanus toxoid conjugates," *J Immun* 127:1011-1018 (1981).

Jennings, et al., in "Seminars in infectious disease," Weinstein, et al., Ed., vol. IV, Chapter 34, pp. 247-253 (1982).

Kaliyaperumal, et al., "Carrier-induced epitope-specific regulation and its bypass in a protein-protein conjugate," *Eur J Immunol* 25:3375-3380 (1995).

Kolb, et al., "Insertion of a foreign gene into the beta-casein locus by Cre-mediated site-specific recombination," *Gene* 227:21-31 (1999).

Konadu, et al., "Synthesis characterization, and immunological properties in mice of conjugates composed of detoxified lipopolysaccharide of *Salmonella paratyphi* A bound to tetanus toxoid with emphasis on the role of O acetyls," *Infect Immun* 64(7):2709-2715 (1996).

Konen-Waisman, et al., "Self and foreign 60-kilodalton heat shock protein T cell epitope peptides serve as immunogenic carriers for a T cell-Independent sugar antigen," *J Immunol* 154:5977-5985 (1995).

Kumar, et al., "Universal T helper cell determinants enhance immunogenicity of a *Plasmodium falciparum* merozite surface antigen peptide," *J Immunol* 148:1499-1505 (1992).

Leclerc, et al., "A synthetic vaccine constructed by copolymerization of B and T cell determinants," *Eur L Immunol* 17:269-273 (1987).

Leiter, "Mice with targeted gene disruptions or gene insertions for diabetes research: problems, pitfalls, and potential solutions," *Diabetologia* 45:296-308 (2002).

Lett, et al., "Immunogenicity of polysaccharides conjugated to peptides containing T- and B-cell epitopes," *Infect Immun* 62(3):785-792 (1994).

Liptak, et al., "Decline of pediatric admissions with *Haemophilus influenza* type b in New Yorl state, 1982 through 1993: Relation to immunizations," *J Pediatrics* 130:923-930 (1997).

Lucas, et al., "Functional Differences in idiotypically defined IgGI anti-polysaccharide antibodies elicited by vaccination with *Haemophilus influenza* type b polysaccharide-protine conjugates," *J Immunol* 154:4195-4202 (1995).

McNamara, et al., "Monoclonal idiotope vaccine against *Streptococcus pneumoniae* Infection," *Science* 226:1325-1326 (1984).

Marburg, et al., "Bimolecular chemistry of macromolecules: synthesis of bacterial polysaccharide conjugates with *Neisseria meningitides* membrane protein," *J Am Chem* 108:5282-5287 (1986).

Moxon, et al., "The role of bacterial polysaccharide capsules as virulence factors," *Curr Top Microbiol Immunol* 150:65-85 (1990).

Panina-Bordignon, et al., "Universally immunogenic T cell epitopes: promiscuous binding to human MHC class II and promiscuous recognition by T cells," *Eur J Immunol* 19:2237-2242 (1989).

Paradiso, et al., "Novel approaches to the development of glycoconjugate vaccines with synthetic peptides as carriers," *Vaccine Res* 2(4):239-248 (1993).

Pesters, et al., "Synthetic trimer and tetramer of 3-beta-D-ribose-(1-1)-D-ribitol-5-phosphate conjugated to protein induce antibody responses to Haemophilus influenzae type b capsular polysaccharide in mice and monkeys," *Infect Immun* 60:1826-1833 (1992).

Robbins, et al., "Prevention of systemic infections, especially meningitis, caused by Haemophilus Influenzae Type b," *JAMA* 276:1181-1185 (1996).

Sad, et al., "Bypass of carrier-induced epitope-specific suppression using a T-helper epitope," *Immunol* 76:599-603 (1992).

Santosham, "Prevention of *Haemophilus influenzae* type b disease," *Vaccine* 11(1):552-557 (1993).

Schneerson, et al., "Preparation, characterization, and immunogeniscity of *Haemopnilus influenzae* type b polysaccharide-protein conjugates," *J exp med* 152:361-376 (1980).

Schneerson, et al., "Quantitative and qualitative analyses of serum antibodies elicited in adults by *Haemophilus influenzae* type b and pneumococcus type 6A capsular polysaccharide-tetanus toxoid conjugates," *Inf Immun* 52(2):519-528 (1986).

Sidman, et al., "Receptor-mediated inactivation of early B lymphocytes," *Nature* 257:149-151 (1975).

Thomsons, et al., "Targeting a polyepitope protein incorporating multiple class II-restricted viral epitopes to the secretory/endocytic pathway facilitates immune recognition by CD4+ cytotoxic T lymphocytes: a novel approach to vaccine design,"*J Virol* 72(3):2246-2252 (1998).

Tunkel, et al., "Pathogenisis and pathophysiology of bacterial meningitis," *Clin Microbio* 6(2):118-136 (1993).

Valmori, et al., Use of human universally antigenic tetanus toxin T cell epitopes as carriers for human vaccination, *J Immunol* 149:717-721 (1992).

Peeters, C. et al. "Effect of Carrier Priming on Immunogenicity of Saccharide-Protein Conjugate Vaccines," Infectin and Immunity, vol. 59, No. 10, 1991, pp. 3504-3510.

Baraldo, K. et al. "N 19 Polyepitope as a Carrierfor Enhanced Immunogenicity and Protective Efficacy of Meningococcal Conjugate Vaccines," Infection and Immunity, vol. 72, No. 8, 2004, pp. 4884-4887.

* cited by examiner

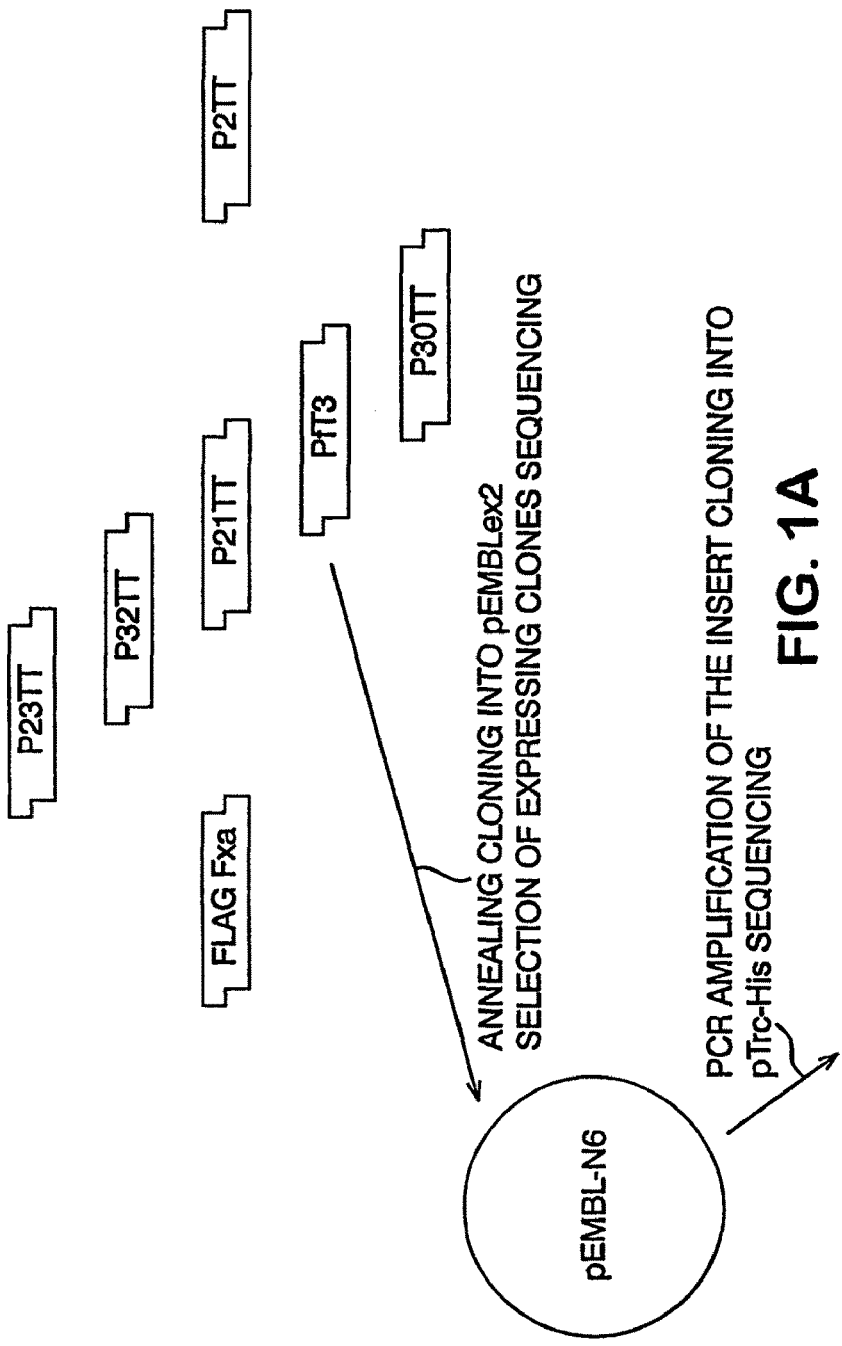
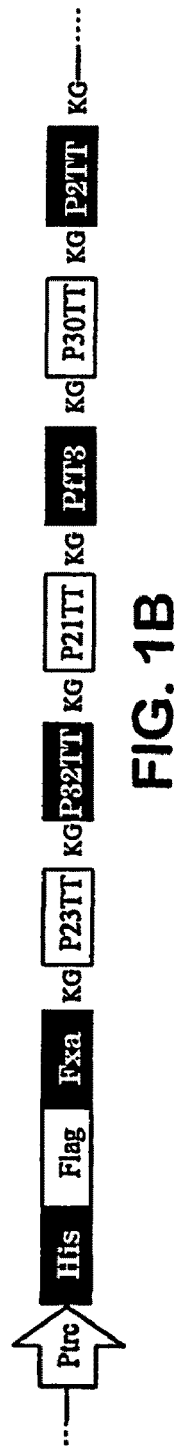
FIG. 1A
FIG. 1B

AAC TCC AAA TTC ATC ATC GGT ATC ACC GAA AAA GGT GGA TCT CCG CAT CAT ACC GCG CTG CGC CAG GCG ATT CTG TGC TGG
Gln Ser Lys Phe Ile Gly Ile Thr Glu Lys Gly Gly Ser Pro His His Thr Ala Leu Arg Gln Ala Ile Leu Cys Trp

GGC GAA CTG ATG ACC CTG GCG AAA GGA TCT CCG AAA TAT GTG AAA CAG AAC ACC CTG AAA CTG GGC G ACC AAA GGA TCG
Gly Glu Leu Met Thr Leu Ala Lys Gly Ser Pro Lys Tyr Val Lys Gln Asn Thr Leu Lys Leu Ala Thr Lys Gly Ser

TTT TTT CTG CTG ACC CGC ATT CCG CAG TCT CTG GAT AAA GGC TAT TCT GGC CCG CTG AAA GCG GAA ATT
Phe Phe Leu Leu Thr Arg Ile Pro Gln Ser Leu Asp Lys Gly Tyr Ser Gly Pro Leu Lys Ala Glu Ile

GCG CAG CGC CTG GAA GAT GTG AAA GGA TCC TAA
Ala Gln Arg Leu Glu Asp Val Lys Gly Ser End

FIG. 2C

```
GGC GAA CTG ATG ACC CTG GCG AAA GGA TCT CCG AAA TAT GTG AAA CAG AAC ACC CTG AAA CTG GCG ACC AAA GGA TCG
GLY GLU LEU MET THR LEU ALA LYS GLY SER PRO LYS TYR VAL LYS GLN ASN THR LEU LYS LEU ALA THR LYS GLY SER

TTT TTT CTG CTG ACC CGC ATT CTG ACC ATT CCG CAG TCT CTG GAT AAA GGC TAT TCT GGC CCG CTG AAA GCG GAA ATT
PHE PHE LEU LEU THR ARG ILE LEU THR ILE PRO GLN SER LEU ASP LYS GLY TYR SER GLY PRO LEU LYS ALA GLU ILE

GCG CAG CGC CTG GAA GAT GTG AAA GGA TCT CAG CCG TCT GTT CAG ATT CAG GGT GAA CGT GAA ATC GCA
ALA GLN ARG LEU GLU ASP VAL LYS GLY SER GLN PRO SER VAL GLN ILE GLN GLY VAL TYR GLN GLY GLU ARG GLU ILE ALA

TCT CAT AAC AAA GGA TCC TAA
SER HIS ASN LYS GLY SER END
```

FIG. 7B

[N19] — KG-P23TT-KG-P32TT-KG-P21TT-KG-P1TT3-KG-P30TT-KG-P2TT-KG-HB VncKG-HA-KG-HBsAg-KG —

```
ATG GGG GGT TCT CAT CAT CAT CAT C

```
TTT TTT CTG CTG ACC CGC ATT CTG ACC ATT CCG CAG TCT CTG GAT AAA GGC TAT TCT GGC CCG AAA GCG GAA ATT
PHE PHE LEU LEU THR ARG ILE LEU THR ILE PRO GLN SER LEU ASP LYS GLY TYR SER GLY PRO LYS ALA GLU ILE

GCG CAG CGC CTG GAA GAT GTG AAA GGA TCT GTT TCC ATC GAC AAA TTC CGT ATC TTC TGC AAA CCG AAC AAA
ALA GLN ARG LEU GLU ASP VAL LYS GLY SER VAL SER ILE ASP LYS PHE ARG ILE PHE CYS LYS ALA ASN PRO LYS

GGT CTG AAA TTC ATC ATC AAA CGT TAC ACC CCG AAC AAC GAA ATC GAC TCC AAA GGT ATC CGT GAA GAC AAC ATC
GLY LEU LYS PHE ILE ILE LYS ARG TYR THR PRO ASN ASN GLU ILE ASP SER LYS GLY ILE ARG GLU ASP ASN ILE

ACC CTG AAA CTG GAC CGT TGC AAC AAC AAA GGT GAA AAG AAG ATC CTG AAA ATG GAA AAA GCT TCT TCT GTT TTC AAC
THR LEU LYS LEU ASP ARG CYS ASN ASN LYS GLY GLU LYS LYS ILE LEU ALA LYS MET GLU LYS ALA SER SER VAL PHE ASN

GTT GTT AAC TCT AAA GGT TTC AAC AAC ACC GTT TCC TTC TGG CTG CGT GTT CCG AAA GTT TCC GCT TCC CAC CTG
VAL VAL ASN SER LYS GLY PHE ASN ASN THR VAL SER PHE TRP LEU ARG VAL PRO LYS VAL SER ALA SER HIS LEU

GAA AAA GGT CAG TAC ATC AAA GCT AAC TCC AAA TTC ATC GGT ATC ACC GAA AAA GGT GGA TCT CCG CAT CAT ACC GCG
GLU LYS GLY GLN TYR ILE LYS ALA ASN SER LYS PHE ILE GLY ILE THR GLU LYS GLY GLY SER PRO HIS HIS THR ALA

CTG CGC CAG GCG ATT CTG TGC TGG GGC GAA CTG ATG ACC CTG GCG AAA GGA TCT CCG AAA TAT GTG AAA CAG AAC ACC
LEU ARG GLN ALA ILE LEU CYS TRP GLY GLU LEU MET THR LEU ALA LYS GLY SER PRO LYS TYR VAL LYS GLN ASN THR

CTG AAA CTG GCG ACC AAA GGA TCG TTT TTT CTG CTG ACC CGC ATT CCG ACC ATT CCG CAG TCT CTG GAT AAA GGA TCC
LEU LYS LEU ALA THR LYS GLY SER PHE PHE LEU LEU THR ARG ILE PRO THR ILE PRO GLN SER LEU ASP LYS GLY SER
```

FIG. 8B

POLYPEPTIDE CARRIER PROTEIN

CROSS-REFERENCE TO RELATED APPLICATIONS

This application is a divisional of U.S. application Ser. No. 11/030,635, filed Jan. 6, 2005, now U.S. Pat. No. 7,538,207, which is a continuation of U.S. application Ser. No. 09/674,183, filed Nov. 14, 2000, now U.S. Pat. No. 6,855,321, from which applications priority is claimed pursuant to 35 U.S.C. §120, which is a national stage application filed under 35 U.S.C. §371 of PCT Application No. PCT/IB99/00844, filed Apr. 27, 1999, which claims foreign priority to GB Application No. 908932.9, filed Apr. 27, 1998, which applications are incorporated herein by reference in their entireties.

TECHNICAL FIELD

The present invention relates to polyepitope carrier proteins. When conjugated to capsular polysaccharides, these carrier proteins are useful as components of vaccines that are capable of eliciting a T-cell dependent immune response. Particularly, the proteins of the present invention may be used to confer protection against infection from encapsulated bacteria in infants between the ages of 3 months and about 2 years.

BACKGROUND

Encapsulated bacteria such as *Haemophilus influenzae*, *Neisseria meningitidis* and *Streptococcus pneumoniae* constitute a significant cause of morbidity and mortality in neonates and infants world-wide (Tunkel & Scheld, 1993). In developing countries, around one million children die each year due to pneumonia alone. Furthermore, even in developed countries, the increase in the phenomenon of antibiotic resistance means that there is a great need to improve on existing vaccines.

The polysaccharide capsule of *H. influenzae*, *N. meningitidis* and *S. pneumoniae* represents a major virulence factor that is important for nasopharyngeal colonisation and systemic invasion by encapsulated bacteria (Moxon and Kroll, 1990). Consequently, much of the research directed toward finding protective immunogens has focused on capsular polysaccharides. The finding that these polysaccharides are able to elicit the formation of protective antibodies led to the development of a number of vaccines that have been efficacious in protecting adults from disease (Andreoni et al. 1993; Goldblatt et al. 1992).

The problem with capsular polysaccharide vaccines developed to date is that they suffer an inherent inability to protect children under two years of age from disease (Holmes and Granoff 1992). This is a significant drawback when it is appreciated that this population of children is at highest risk of infection. Their failure to block infection is believed to derive from the T-cell independent (TI) type of immune reaction that is the only antibody response used by the body against polysaccharide antigens. This type of response does not involve MHC Class II restriction molecules for antigen presentation to T-cells; as a consequence, T-cell help is prevented. Although the TI response works well in adults, it is inactive in very young children due to a combination of factors such as functional B-cell immaturity, inactivation of B-cell receptor-mediated signalling and B-cell anergy in response to antigen stimulation.

To overcome this drawback, two particular vaccine approaches are currently being investigated. The first is the development of anti-idiotype vaccines that contain peptides that mimic carbohydrate idiotypes (McNamara 1984; Agadjanyan, 1997). The second approach involves conjugate vaccines that are designed to transform T-cell independent (TI) polysaccharide antigens into T-dependent (TD) antigens through the covalent linkage of the polysaccharide to a peptide carrier.

*H. influenzae* type B (Hib) conjugate vaccines represent a leading example for the development of other vaccines against infections that are due to capsulated bacteria. In fact, meningitis and other infections caused by Hib have declined dramatically in countries where widespread vaccination with Hib conjugate has been achieved (Robins, 1996). Complete elimination of the pathogen might be possible, but depends upon several factors, including a further improvement of the existing vaccines (Liptak, 1997).

The widely distributed paediatric vaccine antigens tetanus and diptheria toxoids have been selected as carrier proteins with the aim of taking advantage of an already-primed population at the time of conjugate vaccine injection. Previous vaccination with paediatric diptheria-tetanus (DT) or diptheria-tetanus-pertussis (DTP) vaccines means that carrier priming may now be exploited to enhance the immune response to polysaccharide conjugates.

A number of such vaccines have been successfully produced and have been efficacious in reducing the number of deaths caused by these pathogens. The carriers used in these vaccines are large antigens such as tetanus toxoid, non-toxic diptheria toxin mutant CRM197 and group B *N. meningitidis* outer membrane protein complex (OMPC). However, in the future, it is thought that as the number of conjugate vaccines containing the same carrier proteins increases, the suppression of immune responses by pre-existing antibodies to the carrier is likely to become a problem.

Much research is now being directed to the development of improved carrier molecules that contain carrier peptides comprising CD4+ T helper cell (Th) epitopes, but which do not possess T-cell suppressive (Ts) functions (Etlinger et al. 1990). Peptides which retain only helper functions (CD4+ epitopes) are most suitable as carriers, since their effect is sufficient to induce T cell help but the carrier is small enough to limit or to completely avoid production of anti-carrier antibodies.

Various publications demonstrate the ability of such peptides to confer T-cell help to haptens when covalently linked to them (Etlinger, 1990; Valmori 1992; Sadd 1992; Kumar 1992; Kaliyaperumal, 1995; De Velasco, 1995 and Bixler 1989). However, to date, these publications have not resulted in the development of effective vaccines. There thus remains a great need for the development of new, improved vaccine strategies that are effective in combating diseases caused by encapsulated bacteria in infants and young children.

SUMMARY OF THE INVENTION

According to the present invention, there is provided a carrier protein comprising at least five CD4+ T-cell epitopes. Preferably, the carrier protein is conjugated to a polysaccharide. These compounds are useful as immunogenic compounds that may in turn be useful as components of protective vaccines against diseases caused by bacterial pathogens.

A carrier protein is an antigenic polypeptide entity that induces the formation of antibodies directed against an antigen conjugated to it, by the immune system of an organism into which the carrier-antigen conjugate is introduced. The necessity to use carrier proteins results from the fact that although many short epitopes are protective, they are poorly immunogenic. This negates the usefulness of these epitopes in the generation of new and efficacious vaccines. By conjugating an immunogenic carrier protein to a molecule that is non-immunogenic, it is possible to confer the high immunogenicity of the carrier protein onto the conjugate molecule. Such conjugate molecules stimulate the generation of an immune response against the non-immunogenic portion of the conjugate molecule and thus have been effectively used in vaccines that protect against pathogens for which protective immunity could not otherwise be generated.

Hence, highly immunogenic proteins (such as tetanus toxoid) have historically been used as carriers in order to induce a Th cell response that provides help to B cells for the production of antibodies directed against non-immunogenic epitopes. However, overall effectiveness has not been generally achieved with this approach, since the antibody response to a hapten (the epitope) coupled to a carrier protein can be inhibited when the recipient host has been previously immunised with the unmodified carrier protein. This phenomenon is termed epitope-specific suppression and has now been studied in a variety of hapten-carrier systems.

Coupling of bacterial polysaccharides to carrier proteins has been shown to improve the immunogenicity of the polysaccharide and results in antigens with novel characteristics. Furthermore, the coupling of a thymus-independent (TI) polysaccharide to a protein makes the polysaccharide thymus-dependent (TD).

A CD4+ T cell epitope is a peptide epitope that stimulates the activity of those T cells that are MHC Class II restricted. This subset of T cells includes Th cells. Many CD4+ epitopes are well known to those of skill in the art and have been shown to confer T cell help to haptens when covalently attached to them (Etlinger et al, 1990; Valmori 1992; Sadd 1992; Kumar 1992; Kaliyaperumal, 1995).

The CD4+ T epitopes used in the carrier proteins of the present invention ideally comprise peptides that are of as short a length as possible. The epitope will thus retain its characteristics to a sufficient degree to induce T-cell help, yet will be small enough that excessive production of anti-carrier antibodies will be minimised. This is preferable, since it is thought that suppression of immune responses by pre-existing antibodies to carrier epitopes is likely to become a problem in the future if the number of congregate vaccines containing common carrier proteins keeps growing. Furthermore, the use of short peptides as carrier epitopes affords the rational selection of suitable Th epitopes, whilst avoiding stretches of sequence that contain B-cell or T-suppressor epitopes that will be detrimental to the function of the protein in eliciting a TI immune response.

Suitable proteins from which CD4+ epitopes may be selected include tetanus toxin (TT), *Plasmodium falciparum* circumsporozite, hepatitis B surface antigen, hepatitis B nuclear core protein, *H. influenzae* matrix protein, *H. influenzae* haemagglutinin, diphtheria toxoid, diphtheria toxoid mutant CRM197, group B *N. meningitidis* outer membrane protein complex (OMPC), the pneumococcal toxin pneumolysin, and heat shock proteins from *Mycobacterium bovis* and *M. leprae*. The *M. leprae* HSP70 408-427 epitope is not found in the corresponding human homologous sequence (Adams et al., 1997 *Infect Immun,* 65: 1061-70); since a possible limitation in the use of HSP motifs in vaccine formulations is the possibility to induce autoimmune responses due to the high homology between microbial and human HSPs, this epitope is particularly preferred. Other suitable carrier peptide epitopes will be well known to those of skill in the art. The CD4+ T-cell epitopes selected from these antigens are recognised by human CD4+ T cells.

It has been found that the number of T-cell epitopes present in the carrier protein has a significant influence in conferring T-cell help to oligosaccharide molecules conjugated thereto. The polyepitope carrier protein should contain five or more CD4+ T-cell epitopes. Preferably, the polyepitope carrier protein contains between 5 and 50 degenerate CD4+ T-cell epitopes, more preferably between 5 and 20 epitopes, even more preferably 5, 6, 7, 8, 9, 10, 11 or 19 degenerate CD4+ T-cell epitopes. The use of a number of universal epitopes in the carrier protein has been found to reduce the problem of genetic restriction of the immune response generated against peptide antigens.

In addition to CD4+ epitopes, the carrier proteins of the present invention may comprise other peptides or protein fragments, such as epitopes from immunomodulating cytokines such as interleukin-2 (IL-2) or granulocyte-macrophage colony stimulating factor (GM-CSF). Promiscuous peptides (Panina-Bordignon et al 1989), the so-called "universal" peptides (Kumar et al., 1992), cluster peptides (Ahlers et al., 1993) or peptides containing both T cell and B cell epitopes (Lett et al, 1994) may also be used to recruit various effector systems of the immune system, as required.

The polyepitope carrier protein may be produced by any suitable means, as will be apparent to those of skill in the art. Two preferred methods of construction of carrier proteins according to the invention are direct synthesis and by production of recombinant protein. Preferably, the polyepitope carrier proteins of the present invention are produced by recombinant means, by expression from an encoding nucleic acid molecule. Recombinant expression has the advantage that the production of the carrier protein is inexpensive, safe, facile and does not involve the use of toxic compounds that may require subsequent removal.

When expressed in recombinant form, the carrier proteins of the present invention are generated by expression from an encoding nucleic acid in a host cell. Any host cell may be used, depending upon the individual requirements of a particular vaccine system. Preferably, bacterial hosts are used for the production of recombinant protein, due to the ease with which bacteria may be manipulated and grown. The bacterial host of choice is *Escherichia coli*.

Preferably, if produced recombinantly, the carrier proteins are expressed from plasmids that contain a synthetic nucleic acid insert. Such inserts may be designed by annealing oligonucleotide duplexes that code for the CD4+ T-cell epitopes. The 5' and 3' ends of the synthetic linkers may be designed so as to anneal to each other. This technique allows annealing of the oligonucleotides in a random order, resulting in a mixture of potentially different mini-genes comprising any one of a number of possible combinations of epitopes. This mixture is then cloned into any suitable expression vector and a selection process of expressing clones is then performed. This strategy ensures that only those clones are selected that produce a carrier protein that is not detrimental to the health of the cell in which it is expressed. Conversely, arbitrary selection of the order of epitopes has been found to be less successful.

The ends of the epitope-encoding linkers may be designed so that two codons are introduced between the individual epitopes when annealing takes place. Amino acid residues such as glycine or lysine are examples of suitable residues for use in the spacers. In particular, the use of lysine residues in spacers allows the further congregation of carrier protein to capsular polysaccharide. Additionally, the insertion site in the expression plasmid into which the nucleic acid encoding carrier protein is cloned may allow linkage of the polyepitope carrier protein to a tag, such as the "flag" peptide or polyhistidine. This arrangement facilitates the subsequent purification of recombinant protein.

Nucleic acid encoding the polyepitope carrier protein may be cloned under the control of an inducible promoter, so allowing precise regulation of carrier protein expression. Suitable inducible systems will be well known to those of skill in the art and include the well-known lac system (Sambrook et al. 1989).

Methods of recombinant expression of carrier proteins according to the invention will be well known to the skilled artisan, but for the purposes of clarity are briefly discussed herein.

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual*, 2nd ed].

Mammalian viral genes are often highly expressed and have a broad host range; therefore sequences encoding mammalian viral genes provide particularly useful promoter sequences. Examples include the SV40 early promoter, mouse mammary tumour virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognised by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminator/polyadenylation signals include those derived from SV40 [Sambrook et al (1989) "Expression of cloned genes in cultured mammalian cells." In *Molecular Cloning: A Laboratory Manual*].

Some genes may be expressed more efficiently when introns (also called intervening sequences) are present. Several cDNAs, however, have been efficiently expressed from vectors that lack splicing signals (also called splice donor and acceptor sites) [see e.g., Gothing and Sambrook (1981) *Nature* 293:620]. Introns are intervening noncoding sequences within a coding sequence that contain splice donor and acceptor sites. They are removed by a process called "splicing," following polyadenylation of the primary transcript [Nevins (1983) *Annu. Rev. Biochem.* 52:441; Green (1986) *Annu. Rev. Genet.* 20:671; Padgett et al. (1986) *Annu. Rev. Biochem.* 55:1119; Krainer and Maniatis (1988) "RNA splicing." In *Transcription and splicing* (ed. B. D. Hames and D. M. Glover)].

Usually, the above-described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a prokaryotic host for cloning and amplification.

Examples of such mammalian-bacteria shuttle vectors include pMT2 [Kaufman et al. (1989) *Mol. Cell. Biol.* 9:946 and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalised cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

The polynucleotide encoding the protein can also be inserted into a suitable insect expression vector, and is operably linked to the control elements within that vector. Vector construction employs techniques that are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No. 1555* (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.,* 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognised by insect cells, and the signals required for secretion and nuclear accumulation also appear to be conserved between the invertebrate cells and vertebrate cells, leaders of non-insect origin, such as those derived from genes encoding human γ-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of non-fused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome.

Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 □m in size, are highly refractile, giving them a bright shiny appearance that is readily visualised under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* (PCT Pub. No. WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g., Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

Bacterial expression techniques are known in the art. A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolising enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EPO Publ. Nos. 036 776 and 121 775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074].

In addition, a hybrid promoter can also be comprised of a bacteriophage promoter and an *E. coli* operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual]*.

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EPO Publ. No. 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EPO Publ. No. 244 042].

Usually, transcription termination sequences recognised by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EPO Publ. No. 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EPO Publ. Nos. 036 259 and 063 953; PCT Publ. No. WO 84/04541], *Escherichia coli* [Shimatake et al. (1981) *Nature* 292:128; Amann et al. (1985) *Gene* 40:183; Studier et al. (1986) *J. Mol. Biol.* 189:113; EPO Publ. Nos. 036 776, 136 829 and 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with CaCl$_2$ or other agents, such as divalent cations and DMSO. DNA can also be introduced into bacterial cells by electroporation. Transformation procedures usually vary with the bacterial species to be transformed. See e.g., [Masson et al. (1989) *FEMS Microbiol. Lett.* 60:273; Palva et al. (1982) *Proc. Natl. Acad. Sci. USA* 79:5582; EPO Publ. Nos. 036 259 and 063 953; PCT Publ. No. WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Publ. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (eg. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588,684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EPO Publ. No. 324 274). Additional leaders employing an alpha-factor leader fragment that provides for secretion include hybrid alpha-factor leaders made with a presequence of a first yeast, but a pro-region from a second yeast alpha factor. (See e.g., PCT Publ. No. WO 89/02463).

Usually, transcription termination sequences recognised by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognised termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) Gene 8:17-24], pC1/1 [Brake et al. (1984) Proc. Natl. Acad. Sci. USA 81:4642-4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) Proc. Natl. Acad. Sci. USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol, Rev. 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans [Kurtz, et al. (1986) Mol. Cell. Biol. 6:142], Candida maltosa [Kunze, et al. (1985) J. Basic Microbiol. 25:141]. Hansenula polymorpha [Gleeson, et al. (1986) J. Gen. Microbiol. 132:3459; Roggenkamp et al. (1986) Mol. Gen. Genet. 202:302], Kluyveromyces fragilis [Das, et al. (1984) J. Bacteriol. 158:1165], Kluyveromyces lactis [De Louvencourt et al. (1983) J. Bacteriol. 154:737; Van den Berg et al. (1990) Bio/Technology 8:135], Pichia guillerimondii [Kunze et al. (1985) J. Basic Microbiol. 25:141], Pichia pastoris [Cregg, et al. (1985) Mol. Cell. Biol. 5:3376; U.S. Pat. Nos. 4,837,148 and 4,929,555], Saccharomyces cerevisiae [Hinnen et al. (1978) Proc. Natl. Acad. Sci. USA 75:1929; Ito et al. (1983) J. Bacteriol. 153:163], Schizosaccharomyces pombe [Beach and Nurse (1981) Nature 300:706], and Yarrowia lipolytica [Davidow, et al. (1985) Curr. Genet. 10:380471 Gaillardin, et al. (1985) Curr. Genet. 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g., [Kurtz et al. (1986) Mol. Cell. Biol. 6:142; Kunze et al. (1985) J. Basic Microbiol 25:141; Candida]; [Gleeson et al. (1986) J. Gen. Microbiol. 132:3459; Roggenkamp et al. (1986) Mol. Gen. Genet. 202:302; Hansenula]; [Das et al. (1984) J. Bacteriol. 158:1165; De Louvencourt et al. (1983) J. Bacteriol. 154: 1165; Van den Berg et al. (1990) Bio/Technology 8:135; Kluyveromyces]; [Cregg et al. (1985) Mol. Cell. Biol. 5:3376; Kunze et al. (1985) J. Basic Microbiol. 25:141; U.S. Pat. Nos. 4,837,148 and 4,929,555; Pichia]; [Hinnen et al. (1978) Proc. Natl. Acad. Sci. USA 75; 1929; Ito et al. (1983) J. Bacteriol. 153:163 Saccharomyces]; [Beach and Nurse (1981) Nature 300:706; Schizosaccharomyces]; [Davidow et al. (1985) Curr. Genet. 10:39; Gaillardin et al. (1985) Curr. Genet. 10:49; Yarrowia].

Methods for the isolation and purification of recombinant proteins will be well known to those of skill in the art and are summarised, for example in Sambrook et al (1989). Particularly in bacteria such as E. coli, the recombinant protein will form inclusion bodies within the bacterial cell, thus facilitating its preparation. If produced in inclusion bodies, the carrier protein may need to be refolded to its natural conformation. Methods for renaturing proteins to their natural folded state are well known in the art.

Species in which the carrier proteins of the present invention may be immunogenic and thus effective in eliciting an immune response include all mammals, especially humans. In most cases, it will be preferred that the carrier proteins of the present invention are active eliciting an immune response in humans. The population of humans that are in greatest need of protection from disease caused by encapsulated bacteria are infants of between approximately 3 months and 2 years of age. It is during this period that the infants generally do not receive protection from mothers' milk and do not yet possess a sufficiently well-developed immune system themselves to generate an immune response against polysaccharide antigens.

According to a further aspect of the present invention, there are also provided nucleic acid molecules encoding carrier proteins according to the first aspect of the invention. As will be apparent to the skilled artisan, such nucleic acid molecules will be designed using the genetic code so as to encode the epitope that is desired.

Additionally, in order to precisely tailor the exact properties of the encoded carrier proteins, the skilled artisan will appreciate that changes may be made at the nucleotide level from known epitope sequences, by addition, substitution, deletion or insertion of one or more nucleotides. Site-directed mutagenesis (SDM) is the method of preference used to generate mutated carrier proteins according to the present invention. There are many techniques of SDM now known to the skilled artisan, including oligonucleotide-directed mutagenesis using PCR as set out, for example by Sambrook et al., (1989) or using commercially available kits.

Most carrier proteins produced by such techniques of mutagenesis will be less efficacious than wild type proteins. However, it may be that in a minority of cases, such changes produce molecules with improved carrier protein function as desired, such as greater immunogenicity in a certain organism.

The nucleic acid molecules according to this aspect of the present invention may comprise DNA, RNA or cDNA and may additionally comprise nucleotide analogues in the coding sequence. Preferably, the nucleic acid molecules will comprise DNA.

A further aspect of the present invention provides a host cell containing a nucleic acid encoding a carrier protein. A still further aspect provides a method comprising introducing the encoding nucleic acid into a host cell or organism. Introduction of nucleic acid may employ any available technique. In eukaryotic cells, suitable techniques may include calcium phosphate transfection, DNA-dextran, electroporation, liposome-mediated transfection or transduction using retrovirus or other viruses such as vaccinia. In bacterial cells, suitable techniques may include calcium chloride transformation, electroporation or transfection using bacteriophage. Introduction of the nucleic acid may be followed by causing or allowing expression from the nucleic acid, for example by culturing host cells under conditions for allowing expression of the gene.

In one embodiment, the nucleic acid is integrated into the genome of the host cell. Integration may be promoted by the inclusion of sequences that promote recombination with the genome, in accordance with standard techniques (see Sambrook et al., 1989).

According to a further embodiment of the present invention, there is provided a carrier protein comprising at least five CD4+ T-cell epitopes, conjugated to polysaccharide. By polysaccharide is meant any linear or branched polymer consisting of monosaccharide residues, usually linked by glycosidic linkages, and thus includes oligosaccharides. Preferably, the polysaccharide will contain between 2 and 50 monosaccharide unites, more preferably between 6 and 30 monosaccharide units.

The polysaccharide component may be based on or derived from polysaccharide components of the polysaccharide capsule from many Gram positive and Gram negative bacterial pathogens such as *H. influenzae, N. meningitidis* and *S. pneumoniae*. This capsule represents a major virulence factor that is important for nasopharyngeal colonisation and systemic invasion. Other bacteria from which polysaccharide components may be conjugated to the carrier proteins of the present invention include *Staphylococcus aureus, Klebsiella, Pseudomonas, Salmonella typhi, Pseudomonas aeruginosa*, and *Shigella dysenteriae*. Polysaccharide components suitable for use according to this aspect of the present invention include the Hib oligosaccharide, lipopolysaccharide from *Pseudomonas aeruginosa* (Seid and Sadoff, 1981), lipopolysaccharides from *Salmonella* (Konadu et al., 1996) and the O-specific polysaccharide from *Shigella dysenteriae* (Chu et al, 1991). Other polysaccharide components suitable for use in accordance with the present invention will be well-known to those of skill in the art.

Fragments of bacterial capsular polysaccharide may be produced by any suitable method, such as by acid hydrolysis or ultrasonic irradiation (Szn et al, 1986). Other methods of preparation of the polysaccharide components will be well known to those of skill in the art.

The polysaccharide component of the conjugate vaccine should preferably be coupled to the carrier protein by a covalent linkage. A particularly preferred method of coupling polysaccharide and protein is by reductive amination. Other methods include: activation of the polysaccharide with cyanogen bromide followed by reaction with adipic acid dihydrazide (spacer) and by conjugation to carboxide groups of carrier protein using soluble carbodiimides (Shneerson et al, 1986); functionalisation of the carrier protein with adipic acid dihydrazide followed by coupling to cyanogen bromide activated polysaccharides (Dick et al, 1989); chemical modification of both the carrier protein and the polysaccharide followed by their coupling (Marburg et al, 1986; Marburg et al, 1987 and 1989). In some cases, polysaccharides containing carboxide groups such as group C meningococcal polysaccharides can be directly conjugated to proteins using soluble carbodiimides. Polysaccharides can also be activated using alternative agents such as CDAP (1-cyano-4-dimethylamino-pyrridinium tetrafluorborate) and then directly conjugated to the carrier protein (Konadu et al, 1996). Periodate-treated polysaccharides or oligosachrides can all be conjugated to proteins by means of reductive amination (Jennings and Lugowsky, 1982; Anderson, 1983; Insel, 1986). Alternatively, oligosaccharides obtained by acidic hydrolysis can be chemically derivatised by introducing into their reducing end groups an hydrocarbon spacer bearing an active ester terminus; this activated oligosaccharide can be conjugated to the selected carrier protein (Costantino et al, 1992).

The polysaccharide molecule may be coupled to the carrier protein by a spacer molecule, such as adipic acid. This spacer molecule can be used to facilitate the coupling of protein to polysaccharide. After the coupling reaction has been performed, the conjugate may be purified by diafiltration or other known methods to remove unreacted protein or polysaccharide components.

According to a further aspect of the present invention there is provided a method of production of a carrier protein according to the first aspect of the present invention, comprising the steps of:

(a) constructing oligonucleotide molecules that encode peptide epitopes;

(b) annealing the oligonucleotide molecules to form duplexes;

(c) introducing the oligonucleotide duplexes into an expression vector so as to encode a fusion protein;

(d) introducing the expression vector into a bacterial host cell to allow expression of the fusion protein;

(e) isolating the fusion protein produced from a culture of said bacteria.

Optionally, this method may additionally comprise conjugating the carrier protein to a polysaccharide molecule.

Preferably, the bacterial host cell used in this method is an *E. coli* bacterial host cell.

According to the further aspect of the present invention, there is provided a composition comprising a carrier protein that contains at least five CD4+ T-Cell epitopes conjugated to a polysaccharide, in conjunction with a pharmaceutically acceptable excipient. Such a composition may be rationally designed so as to provide protection against disease caused by pathogenic bacteria such as *H. influenzae, S. pneumoniae, N. meningitidis, Staphylococcus aureus, Klebsiella, Pseudomonas* and *S. typhi* and accordingly, may be used as a vaccine. Vaccines according to the invention may either be prophylactic (ie. to prevent infection) or therapeutic (ie. to treat disease after infection).

By pharmaceutically-acceptable excipient is meant any compound that does not itself induce the production of antibodies harmful to the individual receiving the composition. The excipient should be suitable for oral, subcutaneous, intramuscular, topical or intravenous administration. Suitable compounds are typically large, slowly metabolised macromolecules such as proteins, polysaccharides, polylactic acids, polyglycolic acids, polymeric amino acids, amino acid copolymers, lipid aggregates (such as oil droplets or liposomes) and inactive virus particles. Such compounds are well known to those of skill in the art. Additionally, these compounds may function as immunostimulating agents ("adjuvants"). Furthermore, the antigen may be conjugated to a bacterial toxoid.

Preferred adjuvants to enhance effectiveness of the composition include, but are not limited to: (1) aluminium salts (alum), such as aluminium hydroxide, aluminium phosphate, aluminium sulphate, etc; (2) oil-in-water emulsion formulations (with or without other specific immunostimulating agents such as muramyl peptides or bacterial cell wall components), such as for example (a) MF59™ (WO 90/14837), containing 5% Squalene, 0.5% Tween™ 80, and 0.5% SPAN 85 (optionally containing various amounts of MTP-PE, although not required) formulated into submicron particles using a microfluidizer (b) SAF, containing 10% Squalane, 0.4% TWEEN 80, 5% pluronicblocked polymer L121, and thr-MDP either microfluidised into a submicron emulsion or vortexed to generate a larger particle size emulsion, and (c) Ribi™ adjuvant system (RAS), containing 2% Squalene, 0.2% TWEEN 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ may be used or particles generated therefrom such as ISCOMs (immunostimulating complexes); (4) Freund's complete and incomplete adjuvants (CFA & IFA); (5) cytokines, such as interleukins (eg. IL-1, IL-2, IL-4, IL-5, IL-6, IL-7, IL-12, etc.), interferons (eg. IFNγ), macrophage colony stimulating factor (M-CSF), tumor necrosis factor (TNF), etc; and (6) other substances that act as immunostimulating agents to enhance the efficacy of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (eg. the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvanticity effect, as discussed above.

Immunogenic compositions used as vaccines comprise an immunologically effective amount of the carrier protein, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally eg. by injection, either subcutaneously or intramuscularly. They may also be administered to mucosal surfaces (eg. oral or intranasal), or in the form of pulmonary formulations, suppositories, or transdermal applications. Dosage treatment may be a single dose schedule or a multiple dose schedule. The vaccine may be administered in conjunction with other immunoregulatory agents.

As an alternative to protein-based vaccines, DNA vaccination may be employed [eg. Robinson & Torres (1997) *Seminars in Immunology* 9:271-283; Donnelly et al. (1997) *Annu Rev Immunol* 15:617-648]. Accordingly, rather than comprise a peptide, oligopeptide, or polypeptide compound, the vaccines of the invention might comprise nucleic acid encoding these compounds.

According to a further aspect of the invention, there is provided a process for the formulation of an immunogenic composition comprising bringing a carrier protein according to the first aspect of the invention, conjugated to a polysaccharide, into association with a pharmaceutically-acceptable carrier, optionally with an adjuvant.

According to a still further aspect of the present invention, there is provided a method of vaccinating a mammal, preferably a human against a disease, comprising administering to the mammal a composition of carrier protein conjugated to polysaccharide, optionally with a pharmaceutically-acceptable carrier such as an adjuvant.

Various aspects and embodiments of the present invention will now be described in more detail by way of example, with particular reference to the carrier proteins N6 and N10 conjugated to HIB capsular polysaccharide. It will be appreciated that modification of detail may be made without departing from the scope of the invention. All publications, patents, and patent applications cited herein are incorporated in full by reference.

BRIEF DESCRIPTION OF THE FIGURES

FIGS. 1A and 1B show schematic representations of the construction of the N6 protein.

FIGS. 2A, 2B and 2C illustrate the N6 (FIG. 2A) and N10 (FIGS. 2B and 2C) constructs and their respective DNA and amino acid sequences (SEQ ID NOS:13-16). The histidine tag, the flag peptide, the Fxa cutting site and the CD4+ T cell epitopes are underlined.

FIGS. 7A and 7B are is a schematic representations of the N11 construct and its respective DNA and protein sequence (SEQ ID NOS:19-20). The hexahistidine tag, the flag peptide, the FXa cutting site, and the CD4+ T cell epitopes are underlined.

FIGS. 8A and 8B are schematic representations of N19 construct and its respective DNA and protein sequence (SEQ ID NOS:17-18). The hexahistidine tag, the flag peptide, the FXa cutting site, and the CD4+ T cell epitopes are underlined.

FIG. 10A: SDS-Page and Coomassie staining. Analysis of the fractions obtained from IMAC chromatography performed to purify N19 protein. Lane a: prestained molecular weight markers. Lane b: flow through. Lanes from c to m: gradient fractions showing the purified N19 protein; the bands having a molecular weight lower than N19 and visible in the overloaded lanes f, g, and h represents degradation products of the N19 protein.

FIG. 10B: SDS-Page and Coomassie staining. Analysis of the fractions obtained from IMAC chromatography of the N19 conjugated to Hib polysaccharide. All N19 protein resulted to be conjugated, as judged by the high molecular weight of the conjugate and by the absence of 43,000 kDa unconjugated N19 protein.

FIG. 10C: The same conjugate samples used in picture B were subjected to western immuno-blot using an anti-flag antibody. Also here it can be appreciated that all N19 protein migrated as a very high molecular weight after conjugation to Hib polysaccharide, and that there is not unconjugated N19 protein migrating at 43.000 kDa.

DETAILED DESCRIPTION OF THE INVENTION

Materials and Methods

Summary of Standard Procedures and Techniques

Figure 2A:
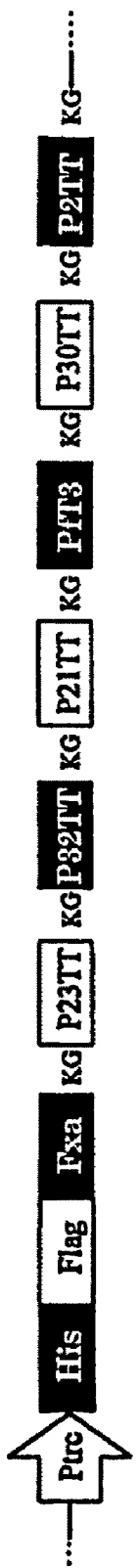

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilised Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Plasmids, Strains and T Cell Clones.

PEMBLex2 plasmid was derived from pEMBL8M (Dente L. and Cortese R., *Meth. Enzymol.* (1987), 155: 111-9) by inserting a $\lambda P_L$ promoter and a polylinker into the EcoRI and HindIII sites. The commercial vectors pTrc-His and pQE30 were purchased from Invitrogen and Qiagen respectively. *E. coli* strains used as recipients of the above plasmids were: K12ΔH1ΔTrp for pEMBLex2, TOP10 for pTrc-His and TG1 for pQE30.

Human T cell clones KSMIK 140 and GG-22 specific for P2TT and P30TT respectively were kindly provided by Dr. A. Lanzavecchia (Basel, Switzerland).

Construction of Recombinant Plasmids that Express the N6 Polyepitope Carrier Protein.

Complementary oligodeoxyribonucleotide pairs coding for P2TT, P21TT, P23TT, P30TT1, P32TT and PfT3 T cell epitopes (Table 1) and for a Flag peptide were synthesised using the DNA synthesiser ABI394 (Perkin Elmer) and the reagents from Cruachem (Glasgow, Scotland). The oligo pairs were separately annealed in T4 DNA ligase buffer (Boehringer Mannheim) and equimolar amounts of each annealing reaction were mixed and ligated at room temperature for 3 hours using T4 DNA ligase (Boehringer Manheim).

The ligase reaction was then loaded onto a 1% agarose gel and subjected to electrophoresis. The bands corresponding to the DNA fragments of expected size were isolated, purified and cloned into the pEMBLex2 expression vector using standard protocols (Sambrook et al., 1989). After transformation, a rabbit antiserum specific for the Flag peptide was used to perform colony-screenings (Sambrook et al., 1989) in order to identify recombinant protein producing clones. Protein extracts from positive clones were analysed using SDS-PAGE to further select for clones on the basis of recombinant protein size.

cloning steps; to the resulting plasmid the HbsAg and MT epitopes were added in a single cloning step.

After DNA sequencing, a correct construct (pTrc-N10) coding for the expected ten epitope polyepitope protein was identified. The N10 coding insert was then transferred from pTrc-N10 to pQE30 (Qiagen) by means of PCR. The sequence of the resulting pQE-N10 construct was then confirmed by DNA sequencing.

Construction of the Recombinant Plasmid Expressing N11 Polyepitope Carrier Protein.

Two complementary oligodeoxyribonucleotides were synthesised and annealed to obtain a DNA linker coding for the HSP70 CD4+ T cell epitope (Table I). The linker was inserted in pTrc-N10 plasmid downstream from N10 coding region and in frame with it. After transformation in TOP10 *E. coli* strain, the transformants were selected using protein expression and DNA sequencing analyses. Glycerol batches of a selected clone (TOP 10/pTrc-N11) having the correct coding sequence and expressing a protein of the expected molecular weight were stored to −80° C.

TABLE I

CD4+ T cell epitopes inserted in the recombinant polyepitope carrier proteins.

| T cell epitope | Amino acid position | Amino acid sequence | SEQ ID NO: | References |
| --- | --- | --- | --- | --- |
| P23TT | 1084-1099 | VSIDKFRIFCKANPK | 1 | Demotz et al. 1993 Eur. J Immunol 23: 425 |
| P32TT | 1174-1189 | LKFIIKRYTPNNEIDS | 2 | Demotz et al. 1993 Eur J Immunol 23: 425 |
| P21TT | 1064-1079 | IREDNNITLKLDRCNN | 3 | Dr. Lanzavecchia, pers. comm. |
| PF T3 | 380-398 | EKKIAKMEKASSVFNVVN | 4 | Hammer et al. 1993 Cell 74: I97 |
| P30TT | 947-967 | FNNFTVSFWLRVPKVSASHLE | 5 | Demotz et al. 1993 Eur. J Immunol 23: 425 |
| P2TT | 830-843 | QYIKANSKFIGITE | 6 | Demotz et al. 1993 Eur. J Immunol 23: 425 |
| HA | 307-319 | PKYVKQNTLKLAT | 7 | Alexander et al. 1994 Immunity 1: 751 |
| HBVnc | 50-69 | PHHTALRQAILCWGELMTLA | 8 | Alexander et al. 1994 Immunity 1: 751 |
| HBsAg | 19-33 | FFLLTRILTIPQSLD | 9 | Greenstein et al. 192 J Immunol 148: 3970 |
| MT | 17-31 | YSGPLKAEIAQRLEDV | 10 | Alexander et al. 1994 Immunity 1: 751 |
| HSP70 | 408-427 | QPSVQIQVYQGEREIASHNK | 11 | Adams et al. 1997 Infect Immun 65: 1061 |
| Flag peptide | | MDYKDDDD | 12 | |

After nucleotide sequencing of the selected clones, a clone named pEMBLN6 was shown to contain six different T cell epitopes with no repetitive sequences. The N6 insert was then PCR-amplified and transferred to pTrc-His expression vector (Invitrogen) using standard techniques (Sambrook et al., 1989). The generation of the N6 expressing plasmids is summarised in FIGS. 1A and 1B.

Construction of Recombinant Plasmids that Express the N10 Polyepitope Carrier Protein Using synthetic oligodeoxyribonucleotides and standard cloning techniques (Sambrook et al., 1989), four additional CD4+ T cell epitopes were added to the N6 protein: HBVnc, HA, HbsAg, and MT (Table I). HBVnc and HA were sequentially introduced into pTrc-N6 by means of two consecutive Construction of Recombinant Plasmids that Express the N19 Polyepitope Carrier Protein.

The DNA fragment encompassing the coding region from P23TT to HBsAg was PCR amplified using the plasmid pTrc-N10 as template and two oligonucleotide primers which allow the insertion of BglII and PstI restriction sites respectively at the 5' and 3' ends of the PCR product. The plasmid pTrc-N10 was digested with BamHI and PstI restriction enzymes and ligated to the PCR product digested with BglII and PstI. After transformation in TOP10 cells and selection of the transformants using protein expression and DNA sequencing analyses, glycerol batches of a selected clone (TOP10/pTrc-N19) having the correct coding sequence and expressing a protein of the expected molecular weight were stored to −80° C.

The pTrc-N19 plasmid was digested with EcoRV and PstI and the insert was cloned in pQE-N10 digested with the same enzymes. After transformation in TG1 cells and selection of the transformants using protein expression and DNA sequencing analyses, glycerol batches of a selected clone (TG1/pQE-N19) having the correct coding sequence and expressing a protein of the expected molecular weight were stored to −80° C.

Purification of the Polyepitope Carrier Proteins.

All the recombinant polyepitope carrier proteins were purified using a similar strategy. Briefly, E. coli cultures were grown in 500 ml LB medium containing 100 µg/ml Ampicillin, at 37° C. At 0.3-0.5 $OD_{600}$, the expression of the polyepitope proteins was induced for 3-5 hours by adding 0.1-1 mM IPTG. Cells were disrupted by sonication or French press, the insoluble fraction was collected by centrifugation, dissolved with buffer A (6 M guanidiniwn-HCL, 100 mM $NaH_2PO_4$, 10 mM Tris base, pH 8) and adsorbed with 2 ml of $Ni^{2+}NTA$ resin (Qiagen).

Then, the resin was packed in a column and washed with buffer A. Guanidinium-HCl was removed from the column by washing with buffer B (8 M Urea, 100 mM $NaH_2PO_4$, 10 mM Tris base) pH 8. After a wash with buffer B pH 6.5, recombinant proteins were eluted with a 20 ml buffer B gradient from ph 6.5 to pH 4. The fractions containing the purified recombinant proteins were pooled and dialysed against PBS, pH 7.2. Proteins were analysed by SDS-PAGE and protein content was determined using the Bradford method. Alternatively, cell pellets obtained from E coli cultures were solubilized by heating at 37° C. in buffer A, the lysates were centrifuged to 15,000 g for 20 min. The supernatants were subjected to column chromatography on NICKEL ACTIVATED CHELATING SEPHAROSE FAST FLOW (Pharmacia). After a wash with buffer A and a wash with buffer B, pH 7, the proteins were separated by collecting fractions from a 0-200 mM gradient of Imidazole in buffer B, pH 7. The fractions containing the purified recombinant proteins (as judged by SDS-PAGE and Coomassie staining) were pooled and dialysed against PBS, pH 7.2.

Preparation and Activation of Hib Oligosaccharides.

The Hib capsular polysaccharide can be prepared according to the protocol described in Gotschlich et al. (1981) *J. Biol. Chem.* 256: 8915-8921.

1.99 L of a 10 mg/ml solution of Hib polysaccharide was hydrolysed in 0.01M acetic acid at 76° C. for 5 hours. After chilling, neutralization and 0.2 µm filtration, the resulting oligosaccharide population had an average degree of polymerisation (avDP) of 8 as measured by the chemical ratio between ribose and reducing groups.

NaCl was then added to the hydrolysate until a concentration of 0.16 M was attained, then diluted 1:1 with 0.16M NaCl/10 mM acetate pH 6 and submitted to tangential flow ultrafiltration on a 10 kDa membrane in order to remove high molecular weight species.

Ultrafiltration comprised approximately 11-fold concentration followed by 15 cycles of diafiltration against 0.16 M NaCl/10 mM acetate, pH 6. The retentate was discarded. The permeate was diluted: 1 with water and 0.22 µm filtered. Chemical analysis revealed an avDp of 8.1.

The permeate obtained from 10 kDa UF was loaded, at a linear flow rate of 150 cm/h, onto a Q-SEPHAROSE FAST FLOW column [10 cm (ID); 5.5 cm (h)] equilibrated with 0.08 M NaCl/0.05 M sodium acetate pH 6. After adsorption, low molecular weight fragments (up to 5 repeats) were removed by washing the column with 10 column volumes of equilibrating buffer and then eluted with 3 column volumes of 0.5 M NaCl/0.005M sodium acetate pH 6. The eluate was 0.2 µm filtered and then analysed for avDp and ion exchange analytical chromatography. AvDP resulted at 17.3, ion exchange analytical chromatography on MONO Q HR 5/5 revealed the absence of any small fragments until DP 5.

To introduce a terminal amino group, reductive amination was then performed; to the fractionated Hib oligosaccharide obtained from Q-SEPHAROSE chromatography, ammonium chloride 35 mg/ml and sodium cyanoboroidride 12 mg/ml final concentrations were added. After stirring, the solution was 0.2 µm filtered and incubated at 37° C. for 120 hours. The amino oligosaccharide was then purified from excess of reagents by precipitation with 95° EtOH (81° final concentration) in the cold for 15-20 hours. The precipitated oligosaccharide was then recovered by centrifugation, solubilized in NaCl 0.4M using approximately ¼ of the starting volume and precipitated again at 81° EtOH in the cold for 15-20 hours.

The amino-oligosaccharide was again recovered by centrifugation and solubilized in about 300 ml of 0.02 M NaCl. After having taken a sample for analysis, the resulting solution was then dried using a rotary evaporator.

Colorimetric amino group analysis confirmed the introduction of a primary amino group into the oligosaccharide.

Derivatisation to active ester was then performed as follows. The amino-oligosaccharide was solubilised in distilled water at a concentration of 40 µmol of amino groups per ml. The solution was then diluted 10-fold with DMSO. Triethylamine was added in molar ratio to the amino groups of 2:1. N-hydroxysuccinimido diester of adipic acid was then added in a molar ratio to the amino groups of 12:1. The reaction mixture was kept under gentle stirring for 2 hours at RT. The activated oligosaccharide was then purified from the excess of reagents by precipitation into 10 volumes of 1-4 dioxane under stirring. After 30 minutes in the cold the precipitate was collected onto a syntered glass filter, washed onto the filter with dioxane and then dried under vacuum. The dried activated oligosaccharide was analysed for its content of active ester groups by a colorimetric method; this test showed the presence of 62.1 µmol of active ester per mg of dried oligosaccharide.

The above-obtained activated oligosaccharide was then used for conjugation experiments.

Conjugation of the Polyepitope Carrier Protein with Hib Capsular Oligosaccharides and Purification of the Conjugates.

33.4 nmoles of recombinant carrier protein and 669 nmoles of activated Hib oligosaccharide in a final volume of 0.5 ml 10 mM phosphate buffer, pH 7, were gently stirred overnight at RT and brought up to 5 ml 1M $(NH_4)2SO_4$, 10 mM phosphate pH7. The sample was subjected to FPLC on a 1 ml PHENYL SEPHAROSE 5/5 HR column (Pharmacia). 1 ml fractions were collected both during washing (1M $(NH_4)2SO_4$, 10 mM phosphate, pH 7) and elution (10 mM phosphate, pH 7). Two peaks corresponding to the non-adsorbed material and to the eluted material were obtained. The pooled fractions corresponding to the non-adsorbed material and the pooled fractions corresponding to the elution peak were subjected to protein and ribose content determination and to SDS-PAGE and Western blot analysis.

A protocol to conjugate recombinant proteins to oligosaccharides directly on $Ni^{2+}$-NTA resin was also developed. Recombinant proteins were purified as described above, but the final dialysis step was omitted. The protein content of the 8M urea fraction pool was measured with the Bradford assay. The pH of the eluted proteins was adjusted to pH8 and adsorption on 1 ml pre-equilibrated $Ni^{2+}$-NTA resin was again performed in a batch mode. Urea was removed by washing with 4×25 ml 100 mM phosphate buffer pH 7.5. The resin was suspended in 1 ml 100 mM phosphate buffer pH 7.5 and a 20-fold molar excess of activated Hib oligosaccharide (as compared to the protein that was adsorbed on the resin) was added to the suspension. The mixture was gently stirred overnight at RT packed in a column, and washed with 50 ml 100 mM phosphate buffer pH 7.5 to remove unconjugated oligosaccharide.

Elution of the conjugate was performed with 100 mM phosphate buffer pH 4. Peak fractions were pooled and dialysed against PBS, pH 7.2. The conjugate was analysed by Coomassie staining of SDS-PAGE gels and Western immunoblot using an anti-flag rabbit antibody. The protein/carbohydrate ratio of the glycoconjugate was determined upon Bradford assay and ribose content determination.

Cultures of PBMCs and T Cell Clones.

Culture medium for PBMCs was RPMI 1640 (Gibco Laboratories, Paisley, Scotland) supplemented with 2 mM L-glutamine, 1% nonessential amino acids, 1 mM sodium pyruvate, gentamycin (50 µg/ml), and 5% human serum (RPMI-HS) or 10% foetal calf serum (RPMI-FCS). For the growth of T-cell lines and clones, RPMI-HS was supplemented with 50 U of recombinant interleukin-2 (rIL-2: Hoffmann La Roche, Nutley, N.J.) per ml.

PBMC Proliferation Assay.

Frozen PBMC ($10^5$) from healthy adults immune to tetanus toxoid were thawed and cultured in duplicate wells of 96-well flat-bottomed microplates, in 0.2 ml of RPMI-HS (Di Tommaso et al, 1997). The recombinant proteins and tetanus toxoids (Chiron, Siena) were added to wells at the final concentration of 10 µg/ml. After 5 days of culture. 1 µCi of [$^3$H] thymidine (specific activity: 5 Ci/mmol, Amersham) was added to each well and DNA-incorporated radioactivity was measured after an additional 16 hrs by liquid scintillation counting.

Proliferation Assay of T Cell Clones.

Two Human T cell clones, KSMIK 140, and GG-22, specific for P2TT and P30TT respectively, and the respective peptides were kindly provided by Dr. A. Lanzavecchia (Basel, Switzerland). T cells ($2\times10^4$) were cultured with autologous irradiated Epstein Barr Virus-transformed B lymphocytes ($3\times10^4$) in 0.2 ml of RPMI-FCS in 96-well flat-bottomed microplates in duplicate wells. Synthetic peptides and conjugated or unconjugated recombinant proteins were added to cultures at a final concentration of 10 µg/ml. After 2 days, 1 µCi of [$^3$H]thymidine was added and the radioactivity incorporated was measured by liquid scintillation counting after an additional 16 hours.

In some experiments, carrier proteins and their conjugates were pre-incubated with APCs for 2-4 hours, then APCs were washed and cultured with T cell clones. This procedure was used to limit possible proteolytic degradation by serum proteases and to be more confident that epitope presentation would be due to intracellularly-processed epitopes.

Immunogenicity Tests.

In a first experiment, equal doses of the glycoconjugates and of the polysaccharide (2.5 µg as polysaccharide) in presence of 0.5 mg of aluminium hydroxide as adjuvant were injected subcutaneously into groups of eight BALB/c and C57BL/6 mice (female, 7-week-old) on days 0, 21 and 35. Mice were bled on day −1 (pre-immune), 20 (pre-2), 34 (pre-3) and 45 (post-3) and individual sera collected and stored at −80° C. before ELISA assay.

In a second experiment, equal doses of the glycoconjugates and of the polysaccharide (2.5 µg as polysaccharide) in the presence of 0.5 mg of aluminium hydroxide as adjuvant were injected subcutaneously into groups of eight Swiss ('D1 and BALB/c mice (female, 7-week-old) on days 0, 10 and 20. A boost of 2.5 µg of purified Hib polysaccharide (HibCPS) in presence of 0.5 mg of aluminium hydroxide was then given to each mouse at day 70. Mice were bled on day −1 (pre-immune). 35 (post-vaccination), 68 (pre-boost) and 85 (post-boost) and individual sera collected and stored at −80° C. before ELISA assay.

In a third experiment, equal doses of CRM-Hib, N10-Hib, and N19-Hib (2.5 µg as polysaccharide) in presence of 0.5 mg of aluminium hydroxide as adjuvant were injected subcutaneously in groups of 6 Swiss CD1 mice (female, 7-week-old) on days 0, 15, and 28 in order to compare the carrier effects. Different groups of mice were also subjected to the same schedule but were previously primed with unconjugated carriers in order to check for potential immunosuppression phenomena. In the latter groups equal doses of carrier proteins (50 µg) in 0.5 mg alum were injected on day −30. All mice were bled on day −32 (pre-priming), −2 (pre-immune), 14 (post-1), 27 (post-2), and 45 (post-3) and the sera were collected and stored to −80° C. before ELISA assay.

ELISA.

NUNC MAXISORP 96-well flat-bottomed plates were coated by overnight incubation at 4° C. with 1 µg/ml (as polysaccharide) of a human serum albumin (HSA) and *H. influenzae* type b polysaccharide conjugate (HSA-Hib). After washing, wells were over-coated using 1% (w/v) gelatin in PBS, pH 7.2 for 3 additional hours at 37° C. Serum samples were diluted 1:50 in 5 mM phosphate buffer, pH 7.2 containing 75 mM NaCL 1% (w/v) BSA and 0.05% (w/v) TWEEN-20 and dispensed in duplicate into the wells. Sera from untreated mice were pooled and diluted 1:50 as above and dispensed into 8 wells. After overnight incubation at 4° C., plates were washed three times with 5 mM phosphate buffer, pH 7.2 containing 75 mM NaCl and 0.05% (w/v) TWEEN-20. Then, alkaline phosphate-conjugated goat IgG anti-mouse IgG diluted 1:1000 and 5 mM phosphate buffer, pH 7.2 containing 75 mM NaCl. 1% (w/v) BSA and 0.05% (w/v) TWEEN-20 were added to each well, and incubated 3 hours at 37° C.

After repeated washing, 100 µl of a chromogen-substrate, p-nitrophenylphosphate, in a diethylenamine solution, were added to each well. Reaction was stopped after 20 min by adding a 4N NaOH solution. Then, the plate was read at 405 mM with a reference wavelength of 595 mM. Titres were expressed as absorbencies at 405 mM ($A_{405mm}$). Mice were considered responders when the average $A_{405mm}$ was found equal to or higher than four times the average of absorbencies of the eight wells with the sera from untreated animals. According to the European Pharmacopoeia [PA/PH/Exp15/T(93)3ANP] four out of eight mice should be responders.

In the second experiment, mice were considered responders when the average $A_{405mm}$ was found four times the average of the absorbencies of eight pre-immune sera of the same group of treatment.

The anti-carrier response was assayed as above described for anti-Hib response using plates coated with N10 or N6 (coating concentration=2 µg/ml).

Results

Construction of the Polyepitope Carrier Proteins.

Using the approaches described in materials and methods, we created several *E. coli* clones expressing different carrier proteins. The following table lists only the six clones we utilised to purify the recombinant polyepitope carrier proteins:

| Name of the clone | Expressed polyepitope protein | Number of amino acids | Theoretic Mol. W. (kDa) | E. coli host strain | Expression vector |
|---|---|---|---|---|---|
| Top10-Trc-N6 | N6 | 143 | 16 | Top10 | pTrc-His |
| Top10-Trc-N10 | N10 | 218 | 24 | Top10 | pTrc-His |
| TG1-QE-N10 | N10 | 218 | 24 | TG1 | pQE30 |
| Top10-Trc-N11 | N11 | 240 | 27 | Top10 | pTrc-His |
| Top10-Trc-N19 | N19 | 390 | 43 | Top10 | pTrc-His |
| TG1-QE-N19 | N19 | 390 | 43 | TG1 | pQE30 |

The clone expressing N6 protein comprised the plasmid pTrc-N6 transformed in the Top10 E. coli strain. As deduced from plasmid DNA sequencing, this plasmid coded for a protein having an hexahistidine amino terminal tail followed in sequence by a flag peptide, a FXa site, and the following T cell epitopes: P23TT, P32TT, P21TT, PfT3, P30TT, and P2TT. All the epitopes were spaced by a KG amino acid sequence (FIG. 2A).

Figure 2B:

The two clones that produced N10 protein were the Top10 E. coli strain containing the plasmid pTrc-N10, and the TGI E. coli strain containing the plasmid pQE-N 10. Both these clones contained the N6 coding sequence fused to a carboxy terminal sequence coding for four additional T cell epitopes which were in the order: HBVnc, HA, HBsAg, and MT (FIGS. 2B-2C).

Figure 7A:
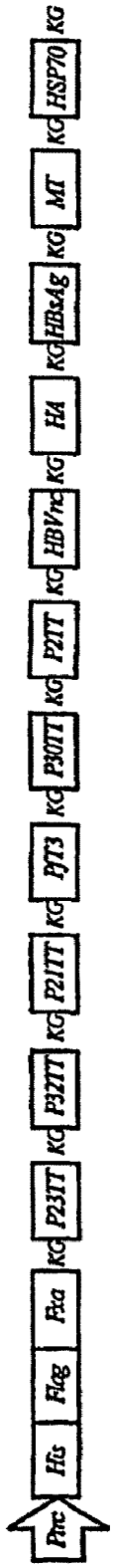

The clone that produced N11 protein comprised the plasmid pTrc-N10 transformed in the Top10 E. coli strain. As deduced from plasmid DNA sequencing, this plasmid coded for a protein consisting in the N10 sequence fused to a carboxy terminal sequence coding for the HSP70 T cell epitope (FIGS. 7A-7B).

The two clones that produced N19 protein were the Top10 E. coli strain containing the plasmid pTrc-N19, and the TG1 E. coli strain containing the plasmid pQE-N19. Both these clones contained the N10 coding sequence fused to a carboxy terminal sequence coding for nine additional T cell epitopes which were in the order: P23TT, P32TT, P21TT, PfT3, P30TT, P2TT, HBVnc, HA, and HBsAg (FIG. 8).

Protein Expression and Purification.

Figure 4:
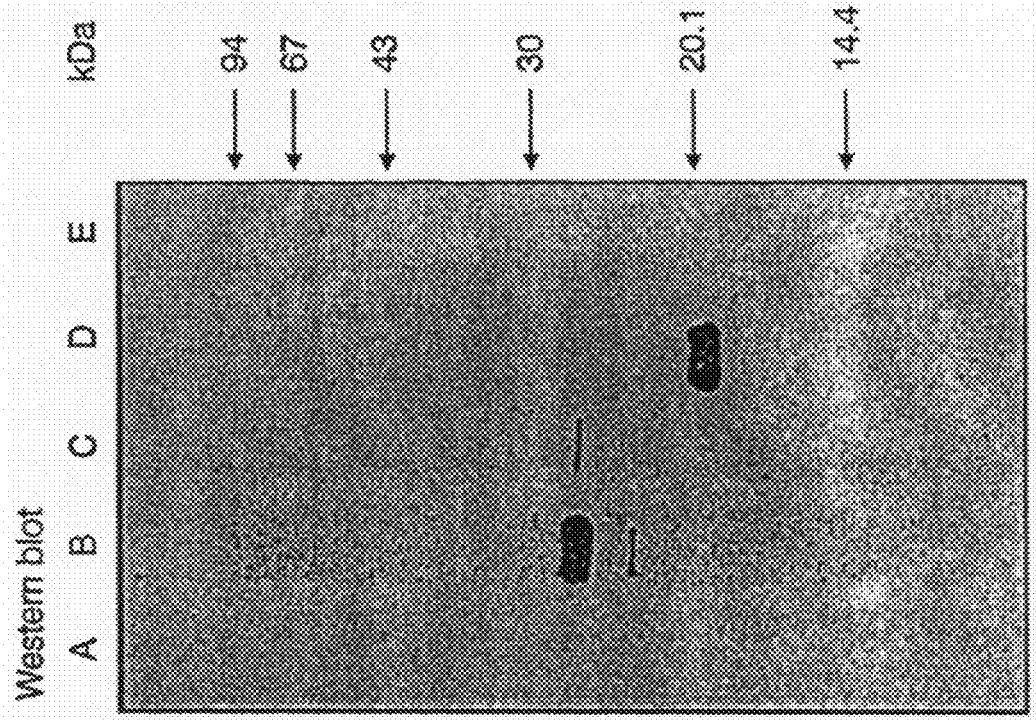
FIG. 4 is an immunoblot of the SDS-PAGE gel that is illustrated in FIG. 3. The Western blot was incubated with a rabbit antiserum specific for the flag peptide and then with a peroxidated anti-rabbit IgG antibody. The immune reaction was then revealed using 4-chloro-1-napthol as substrate for the peroxidase.
Figure 3:
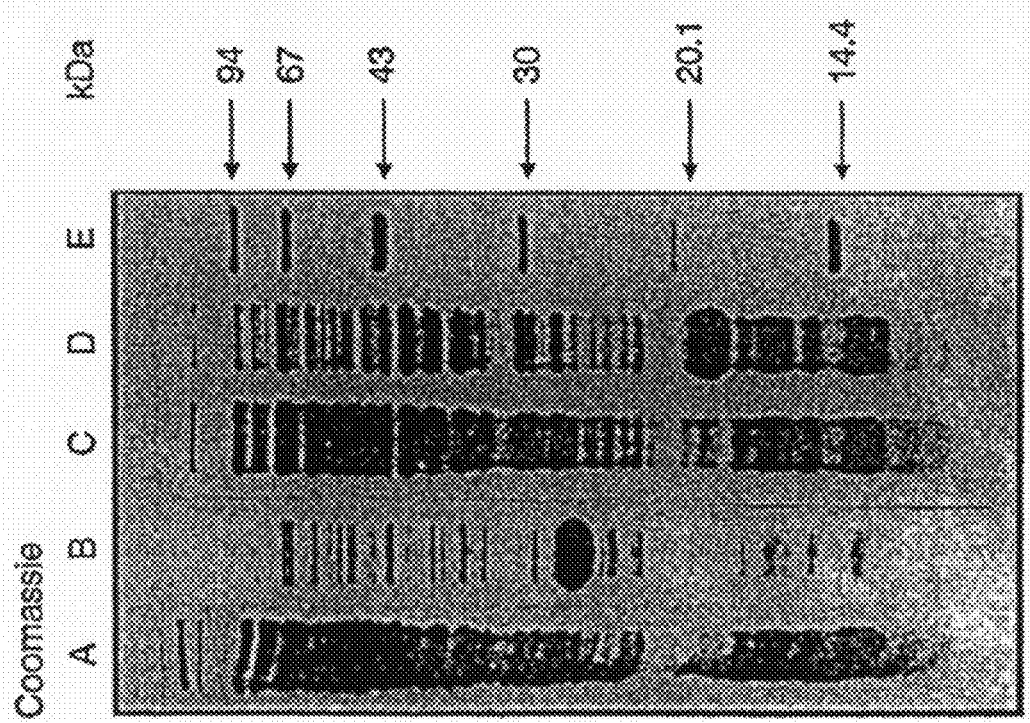
FIG. 3 is a Coomassie-stained SDS-PAGE gel of total protein extracts prepared from induced *E. coli* clones producing the different polyepitope proteins. Lane A: negative control (TG1 cells containing pQE30 vector with no insert); lane B: TG1 cells containing the pQE30-N10 plasmid; lane C: TOP10 cells containing the pTrc-N10 plasmid; lane D: TOP10 cells containing the pTrc-N6 plasmid; lane E: low molecular weight markers.

FIGS. 3 and 4 depict protein expression of the three synthetic proteins. The addition of four new epitopes (HBVnc, HA, HbsAg, and MT) to N6 in pTrc-His (lane D) to obtain N10 protein (lane C) resulted in a remarkable reduction of protein expression. An attempt to increase the expression level of N10 simply involved changing the expression vector (from pTrc)-His to pQE30) and the E. coli strain (from Top10 to TG1). As seen in FIGS. 3 and 4, the amount of N10 expressed by pQE30-N10 in TG1 (lane B) was notably higher than the same protein expressed by pTrc-N10 (lane C). This is thought possibly to be due to the fact that whereas N6 protein was effectively assembled by the E. coli strain in the order of epitopes most suited to the organism, whereas the addition of four further epitopes was effectively forced and thus was less natural. However, the fact that the level of N10 expression was notably increased by simply changing expression vector (from pTrc-His to PQE30) and E. coli strain (from TOP-10 to TG1) suggests that additional factors, other than epitope combination, play a role in protein expression.

Figure 9:
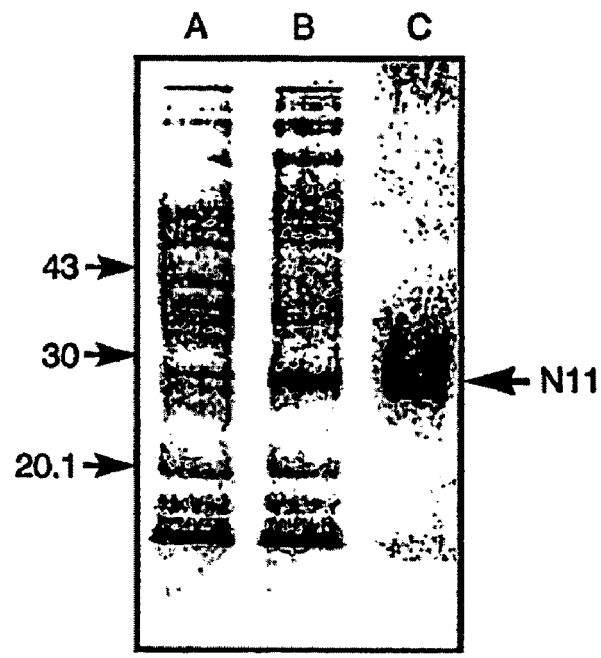
FIG. 9 is an SDS-Page and Coomassie staining of proteins coming from Top10-Trc-N11 *E. coli* clone.
Lane A: Total extract of an uninduced culture.
Lane B: Total extract of a culture induced using IPTG.
Lane C: purified N11 protein (solubilisation of whole cells with guanidinium and IMAC chromatography).

FIG. 9 shows protein expression and purification of the N11 protein (SDS-PAGE and Coomassie staining). Total extract coming from an induced culture (lane B) shows an induced band, corresponding roughly to the expected molecular weight of N11 protein, that is not present in uninduced extract (lane A). The identity of the induced band was established also by western blot using an anti-flag antibody, and was also deduced from plasmid DNA sequencing (FIG. 7). N11 purification (FIG. 9, lane C) was done by solubilising whole cell pellets in guanidinium and by subjecting the whole extract to IMAC chromatography, with this procedure we obtained 14 mg of recombinant N11 protein from one litre of Top10-Trc-N11 flask culture. The addition of HSP70 T cell epitope to the carboxy terminus of N10 resulted in a construct (pTrc-N11) that was able to notably improve the expression of the polyepitope protein as compared to the expression obtained from pTrc-N10.

Figure 10A:
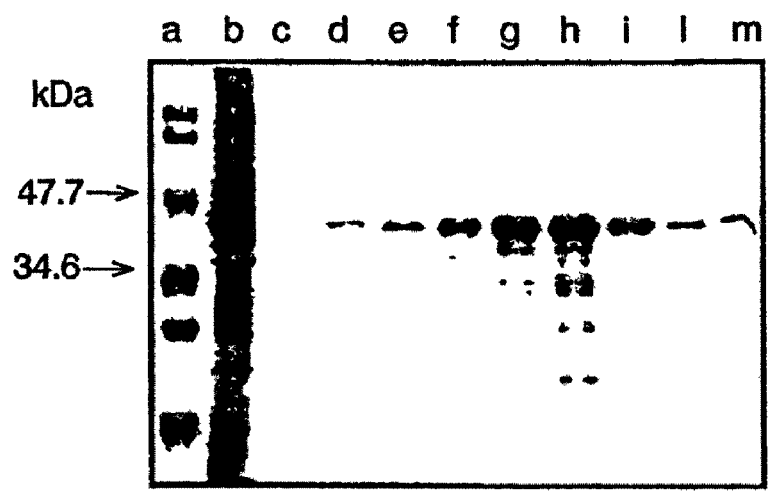
FIGS. 10A, 10B and 10C depict SDS-PAGE gels obtained from IMAC chromatography performed on N19 protein (FIG. 10A) and N19 protein conjugated to Hib polysaccharide (FIG. 10B), and western immunoblots of the N19 protein and the N19 protein conjugated to Hib polysaccharide using an anti-flag antibody (FIG. 10C) as follows.

As it was for the N10 protein, also the expression of N19 protein was improved by charging the expression vector (from pTrc-His to pQE30) and the host strain (from Top10 to TG1). TGI(QE-N19) was used to purify N19 polyepitope protein. By subjecting solubilised inclusion bodies to IMAC chromatography, we purified (see FIG. 10A) 5.42 mg of N19 protein from one litre of flask culture. The identity of N19 was identified in SDS-Page as an induced band having the expected molecular weight, in immuno western blot using an anti-flag antibody, and was also deduced after plasmid DNA sequencing (FIGS. 8A-8B).

All clones expressing recombinant polyepitope proteins produced them mainly in the form of inclusion bodies. Purification of N6 and N10 proteins from inclusion bodies solubilised with 8M urea using an immobilised metal affinity chromatography (IMAC) procedure in the presence of 8M urea resulted in the loss of a high percentage of protein which was elutable with a 6.5-4 pH gradient (data not shown).

Figures 5, 6:
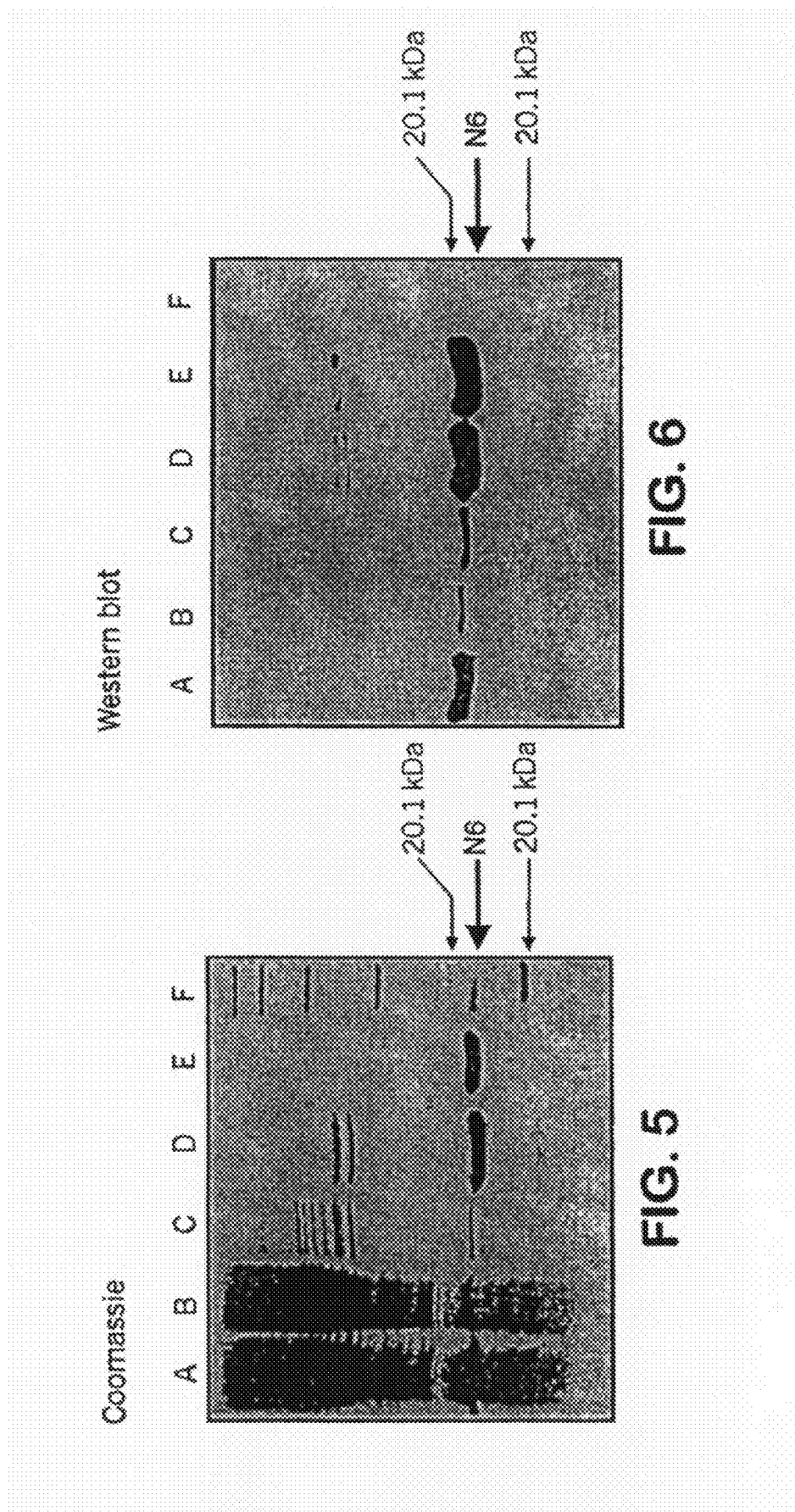
FIG. 5 is an SDS-PAGE Coomassie-stained gel containing different samples obtained during the procedure of purification of the N6 protein. Lane A: starting material (total protein of the induced TOP10 *E. coli* cells containing pTrc-N6 plasmid; lane B: soluble proteins (supernatant obtained after centrifugation of the total protein sample); lane C: proteins soluble in 1M urea (supernatant obtained after washing the insoluble proteins with 1M urea); lane D: inclusion bodies (pellet obtained after washing the insoluble proteins with 1M urea); lane E: N6 protein obtained from purification on $Ni^{2+}$ NTA resin using the immobilised metal affinity chromatography (IMAC) technique; lane F: low molecular weight markers.
FIG. 6 is an immunoblot of the SDS-PAGE gel that is illustrated in FIG. 5. The Western blot was incubated with a rabbit antiserum specific for the flag peptide and then with a peroxidated anti-rabbit IgG antibody. The immune reaction was then revealed using 4-chloro-1-napthol as substrate for the peroxidase.

On the contrary, almost all of the histidine-tagged protein was eluted with the 6.5-4 pH gradient when starting inclusion bodies were solubilised with 6M guanidine hydrochloride (FIGS. 5 and 6). Using this protocol 7.8 mg of N6 was purified from a litre of culture. The N10 protein that was employed in immunisation and T cell proliferation experiments was purified from pTrc-N10 clone.

Given the lower expression of recombinant protein shown by this clone we decided to purify N10 protein by solubilising whole cells with guanidinium in such a way as to exploit soluble and insoluble (inclusion bodies) proteins for IMAC purification. With this procedure 1.5 mg of purified N10 protein was obtained from a litre of culture. The higher success of solubilisation using 6M guanidium is thought to be due to the ability of this compound to solubilise the carrier proteins in monomeric form.

Hib Oligosaccharide Conjugation to Polyepitope Proteins.

Using the phenyl sepharose FPLC protocol we obtained a purified N6-Hib conjugate having a protein content of 79.4 µg/ml, and an oligosaccharide content of 42.7 µg/ml.

We observed that 30% of conjugated protein was unable to bind to phenyl sepharose in the presence of 1M $(NH_4)_2SO_4$. In addition, 30-40% of carrier protein was previously lost during a dialysis step to remove urea before the conjugation reaction. To overcome these problems it was checked if it was possible to perform the conjugation reactions when the protein was adsorbed on the $Ni^{2+}$-NTA resin. We observed that the Hib oligosaccharide was unable to bind $Ni^{2+}$-NTA resin at any pH, suggesting the feasibility of this approach and predicting that no interference due to the oligosaccharide could influence the elution of the protein once conjugation had taken place.

A reaction was thus set up involving protein adsorption on $Ni^{2+}$-NTA resin in the presence of 8M urea, urea removal, conjugation with oligosaccharide, washing, and conjugate elution. No aggregation phenomena were observed for the eluted conjugate. Using this procedure we obtained a purified N6-Hib conjugate having a protein content of 320 μg/ml and an oligosaccharide content of 370 μg/ml. and a purified N10-Hib having a protein content of 113 μg/ml and an oligosaccharide content of 114 μg/ml.

By using a 1:10 protein to carbohydrate molar ratio to conjugate oligosaccharide to recombinant carriers, we observed that a fraction of protein remained unconjugated (as judged by Coomassie staining of SDS-PAGE gel and Western immunoblot; data not shown). When a 1:20 protein to carbohydrate stoichiometric ratio was used, all the purified recombinant proteins were found to be completely conjugated, in fact, by analysing Coomassie-stained gels and western immunoblots using an anti-Flag antibody. We observed that after conjugation of N6 and N10 with Hib oligosaccharides these molecules increased their molecular weight, appearing as a high molecular weight smear, and proteins were no longer visible at the expected molecular weight for N6 and N10 monomers. This suggested that the synthetic proteins were completely conjugated to Hib oligosaccharides (data not shown).

Figure 10B:
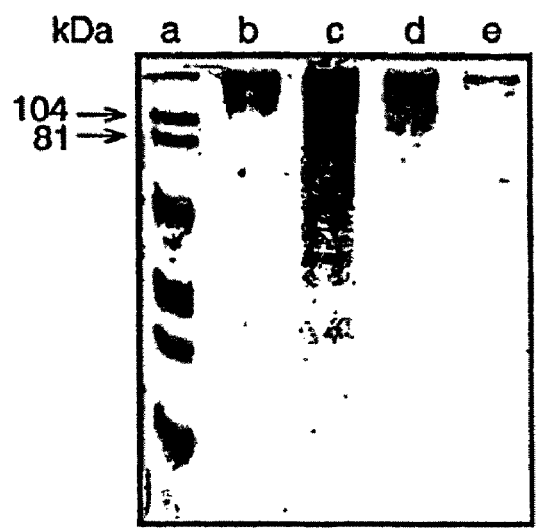
Figure 10C:
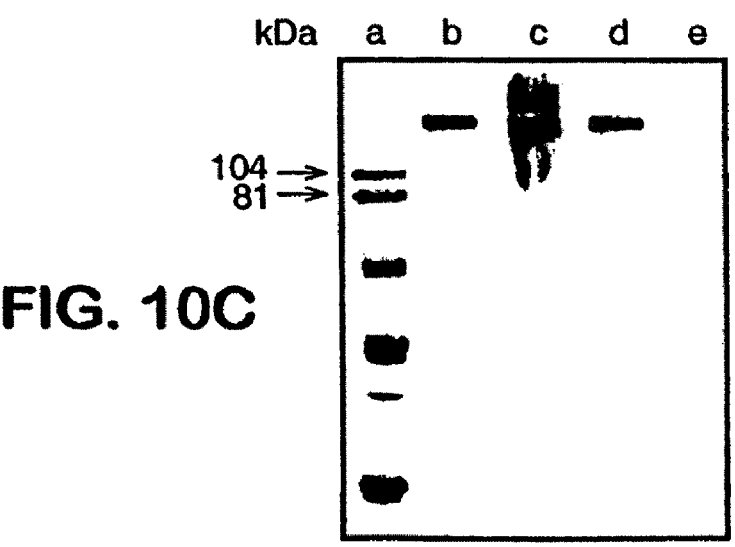

The conjugation of activated Hib oligosaccharide to N19 protein resulted in a protein content of 173 μg/ml and in an oligosaccharide content of 127 μg/ml. FIG. 10B depicts an SDS-Page and Coomassie staining analysis of the fractions obtained from IMAC chromatography of the N19 conjugated to Hib polysaccharide. All N19 protein resulted to be conjugated, as judged by the high molecular weight of the conjugate and by the absence of 43,000 kDa unconjugated N19 protein. FIG. 10C shows the corresponding western immunoblot using an anti-flag antibody. Also here it can be appreciated that all N19 protein migrated as a very high molecular weight after conjugation to Hib polysaccharide, and that there is not unconjugated N19 protein migrating at 43,000 kDa.

Recognition of Carrier Proteins and their Conjugates by Human T Lymphocytes.

Figure 11:
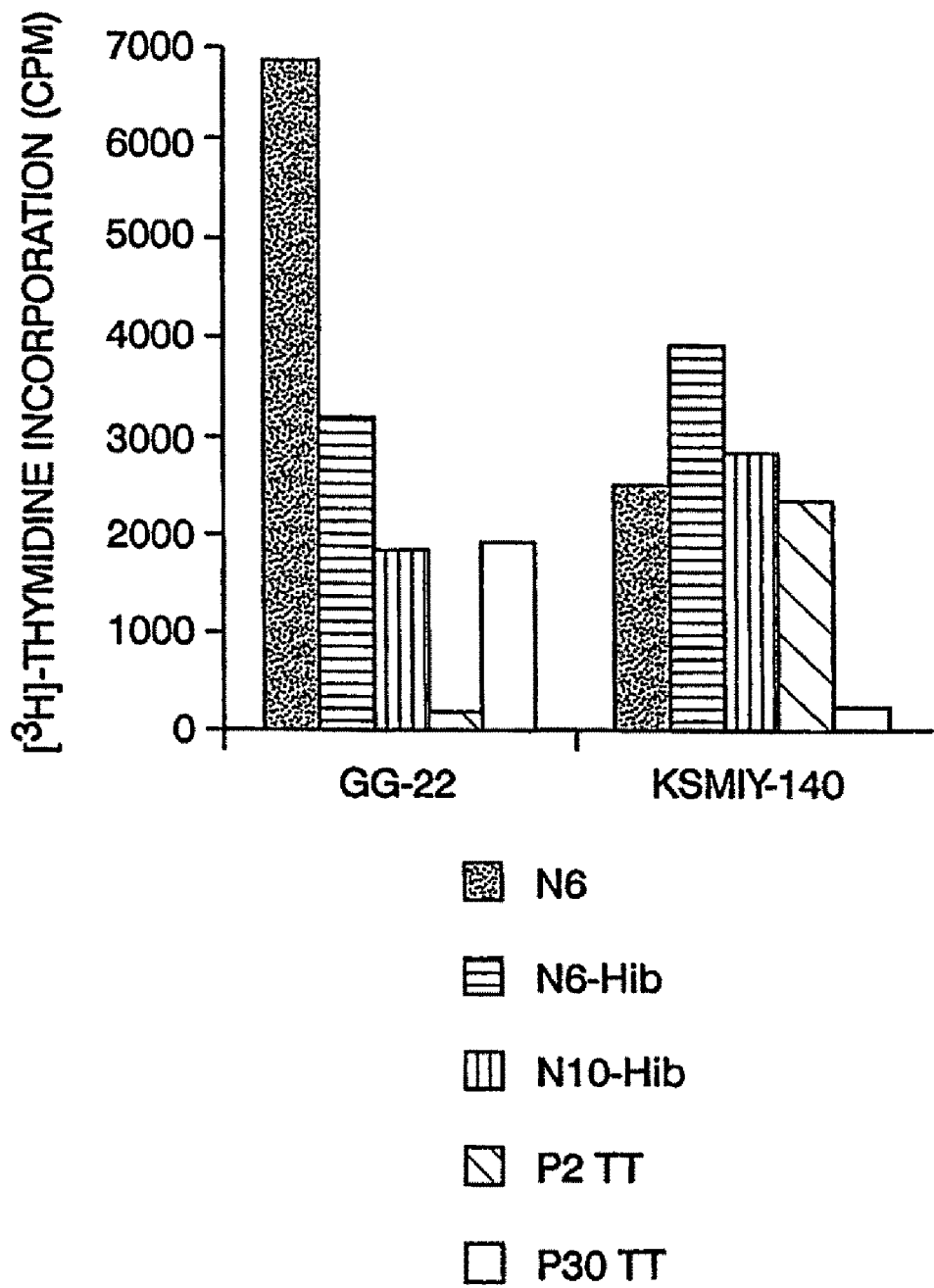
FIG. 11: Proliferative response of two human T cell clones specific for P30TT (GG-22 clone) and P2TT (KSIMK-140 clone) after stimulation with the respective synthetic peptides (controls) and with conjugated or nunconjugated polyepitope proteins (cpm: counts per minute).

To investigate whether T cell epitopes contained in the polypeptides were recognised by human T cells we used T cell clones specific for the TT universal epitopes p2TT and p30TT (Demotz et al. 1993). FIG. 11 shows that N6 is recognised by both clones not only as a simple polypeptide but also after it has been conjugated with polysaccharide. Remarkably, N6-Hib is recognised even better than unconjugated N6 by the T cell clone specific for P2TT. N10-Hib is recognised by the clone specific for p2TT but is poorly recognised by the clone specific for P30TT. In both cases N10-Hib exerts the same stimulatory activity as the synthetic peptide. The N10 clone was not tested in these experiments.

Figure 12:
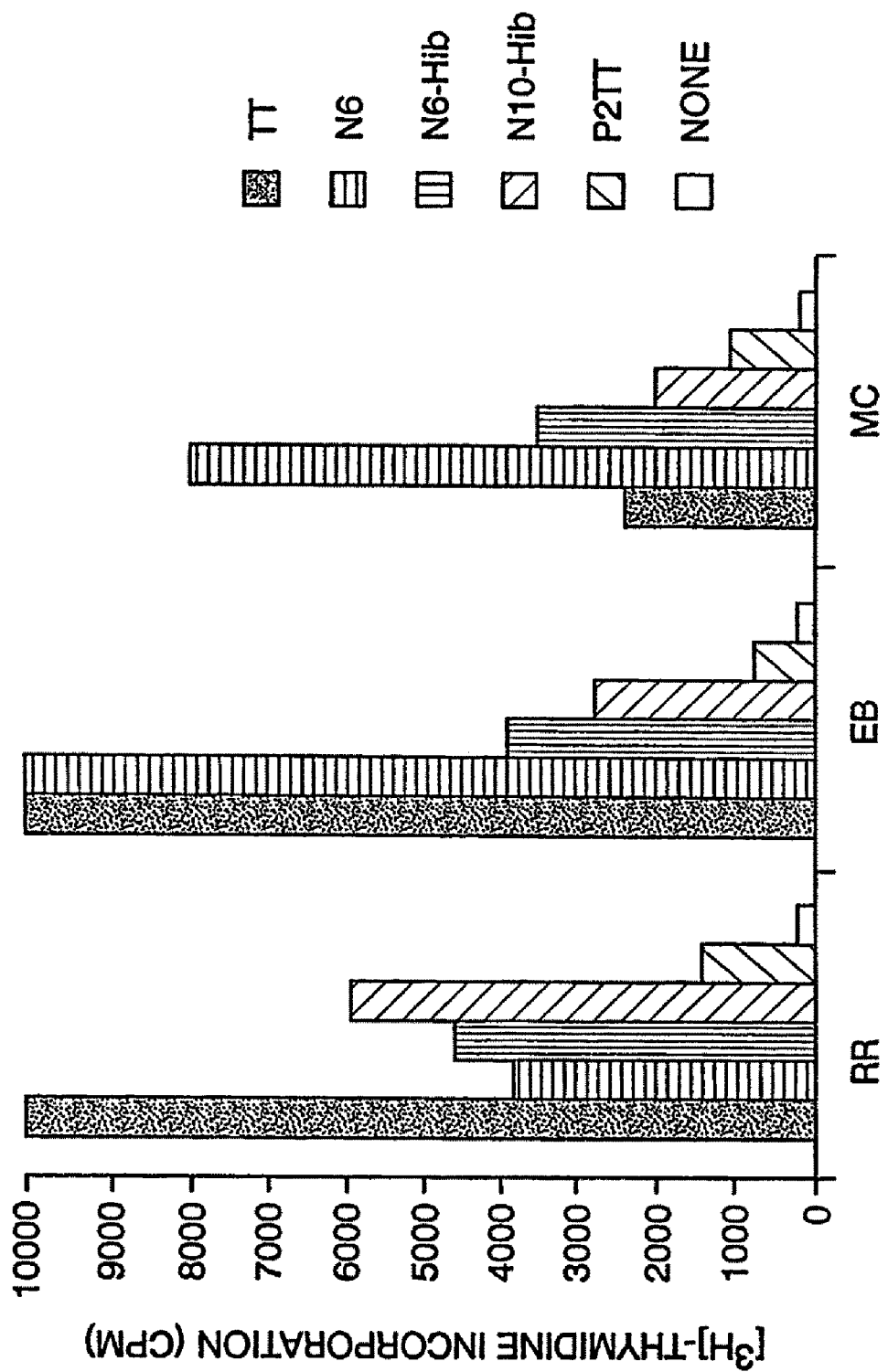
FIG. 12: Peripheral blood mononuclear cells (PBMC) proliferation assay. PBMC from three healthy donors, RR, EB and MC, immune to tetanus toxoid were stimulated with tetanus toxoid, P2TT, N6, N6-Hib and N10-Hib.

Once assessed that the T cell epitopes contained in the carrier proteins are correctly presented to T lymphocytes, we asked whether these carriers maintain their stimulatory capacity when presented to a heterogeneous population of lymphocytes such as PBMC. This could be predictive of whether our carriers might function as such once injected into subjects immune to antigens whose epitopes are included in the carriers themselves. For this purpose we used PBMC from donors immune to TT (A. Di Tommaso et al. 1997), since TT epitopes are the most represented in our polypeptides. FIG. 12 shows that all the formulations were able to stimulate PBMC proliferation.

However, the incubation of PBMC with a synthetic peptide representing one of the epitopes included in both N6 and N10 constructs failed to exert a stimulatory effect. As a positive control, the PBMC were also incubated with 10 μg/ml of TT, that in all cases induced a proliferative response. Interestingly, the N6 polyepitope protein turned out to be the most potent PBMC stimulator among those tested in two out of three volunteers.

Immunogenicity Tests.

The carrier effect of the proteins N10 and N6 in comparison with CRM197 was assayed in mice in several glycoconjugate vaccines. Once coupled to Hib oligosaccharides the carrier proteins were injected in different mouse strains to verify the potential of their carrier effect. In BALB/c mice, an equivalent anti-Hib response was found when CRM197 and N10 were used as carrier proteins, whilst a lower response was found when N6 was used as carrier protein. This result was evident when the results were expressed using titres, while responder percentages failed to evidence the lower anti-Hib response obtained with the N6 protein carrier.

In C57BL/6 mice, the N6 protein gave a negative result, while positive results were obtained with CRM197 and N10, even if to a lower extent. These results were evident both using titres or responder percentages to express the results. When the results were expressed as a responder percentage, the high carrier effect of CRM197 and N10 was well evidenced with respect to N6, whose results were lower than 50% at day −34 and day −45 bleedings, after a comparable primary response (pre-2 bleeding, day 20).

Table II reports the results of the experiments in BALB/c and C57BL/6 mice.

In Swiss CDI mice, the titres obtained with the N10 carrier protein were equivalent to those obtained with CRM197. The anti-Hib titres increased after immunisation up to the 70th day, when a polysaccharide boost was given to assay whether or not an immunological memory was induced in the treated mice. No boost effect was observed with any carrier, although when CRM197 or N10 were used as carrier protein the titre did not decrease. In this mouse strain the immunisation with N6-Hib glycoconjugate give results very similar to the controls (polysaccharide and alum). The boost effect was not evidenced even in BALB/c mice that evoke a lower response with respect to Swiss CD1 mice.

The results are summarised in Table III.

Immunisation of different mice strains with Hib oligosaccharides conjugated to the artificial carrier proteins resulted in a good carrier effect exerted by N10, whilst N6 gave unsatisfactory results. This suggests that the size of the protein or the number of T cell epitopes has a high influence in providing T cell help to the oligosaccharides.

We used outbred CD1 mice to perform an immunogenicity experiment in which the carrier effect of N19 protein was compared to the carrier effects of N10 and CRM197. In addition, in order to explore potential carrier-induced immunosuppression phenomena, the three doses of N10-Hib, N19-Hib and CRM-Hib were given to groups of mice that did not received carrier priming and to groups of mice that one month before were primed with 50 μg of the respective unconjugated carrier (see materials and methods).

TABLE II

| DAY | BLEEDING | RESPONDER (%) | | | $A_{405} \times 1000$ (GMT's) | | |
|---|---|---|---|---|---|---|---|
| | | N10-Hib | N5 + 146-Hib | CRM-Hib | N10-Hib | N5 + 146-Hib | CRM-Hib |
| | | BALB/c MICE | | | | | |
| 0 | PRE-IMMUNE | 0 | 0 | 0 | 10 | 17 | 12 |
| 20 | PRE-2 | 33.3 | 33.3 | 50 | 135 | 162 | 257 |
| 34 | POST-2/PRE-3 | 100 | 100 | 100 | 2022 | 1356 | 1969 |
| 45 | POST-3 | 100 | 100 | 100 | 1717 | 1368 | 1616 |
| | | C57BL/6 MICE | | | | | |
| 0 | PRE-IMMUNE | 0 | 0 | 0 | 28 | 38 | 31 |
| 20 | PRE-2 | 83.3 | 83.3 | 83.3 | 136 | 192 | 609 |
| 34 | POST-2/PRE-3 | 83.3 | 33.3 | 100 | 1451 | 306 | 2612 |
| 45 | POST-3 | 100 | 33.3 | 100 | 1731 | 222 | 2240 |

TABLE III

SWISS CD1 MICE

| DAY | BLEEDING | CRM-Hib | N5 + 146-Hib | N10-Hib | PsHib | ALUM |
|---|---|---|---|---|---|---|
| | | TITRE GMT's ($A_{405nm} \times 10^3$) | | | | |
| -1 | PRE-IMMUNISATION | 59 | 98 | 156 | 166 | 175 |
| 35 | POST-IMMUNISATION | 1577 | 471 | 1007 | 227 | 243 |
| 68 | PRE-BOOST | 2082 | 889 | 1789 | 590 | 461 |
| 85 | POST-BOOST | 2073 | 630 | 1767 | 364 | 479 |
| | | RESPONDER (%) | | | | |
| -1 | PRE-IMMUNISATION | 0 | 0 | 0 | 0 | 0 |
| 35 | POST-IMMUNISATION | 100 | 50 | 62.5 | 0 | 0 |
| 68 | PRE-BOOST | 87.5 | 87.5 | 100 | 25 | 25 |
| 85 | POST-BOOST | 87.5 | 62.5 | 85.7 | 12.5 | 37.5 |

The schedule of the experiment was the following:

| | Days | | | | | | | | |
|---|---|---|---|---|---|---|---|---|---|
| Group | -32 | -30 | -2 | 0 | 14 | 15 | 27 | 28 | 45 |
| 1 | bleeding | DT* | bleeding | CRM-Hib | bleeding | CRM-Hib | bleeding | CRM-Hib | bleeding |
| 2 | bleeding | | bleeding | CRM-Hib | bleeding | CRM-Hib | bleeding | CRM-Hib | bleeding |
| 3 | bleeding | N10 | bleeding | N10-Hib | bleeding | N10-Hib | bleeding | N10-Hib | bleeding |
| 4 | bleeding | | bleeding | N10-Hib | bleeding | N10-Hib | bleeding | N10-Hib | bleeding |
| 5 | bleeding | N19 | bleeding | N19-Hib | bleeding | N19-Hib | bleeding | N19-Hib | bleeding |
| 6 | bleeding | | bleeding | N19-Hib | bleeding | N19-Hib | bleeding | N19-Hib | bleeding |

*For priming we used a chemically detoxified diphtheria toxin (DT: diphtheria toxoid) instead of the non toxic mutant (CRM-197) of diphtheria toxin.

Figure 13:
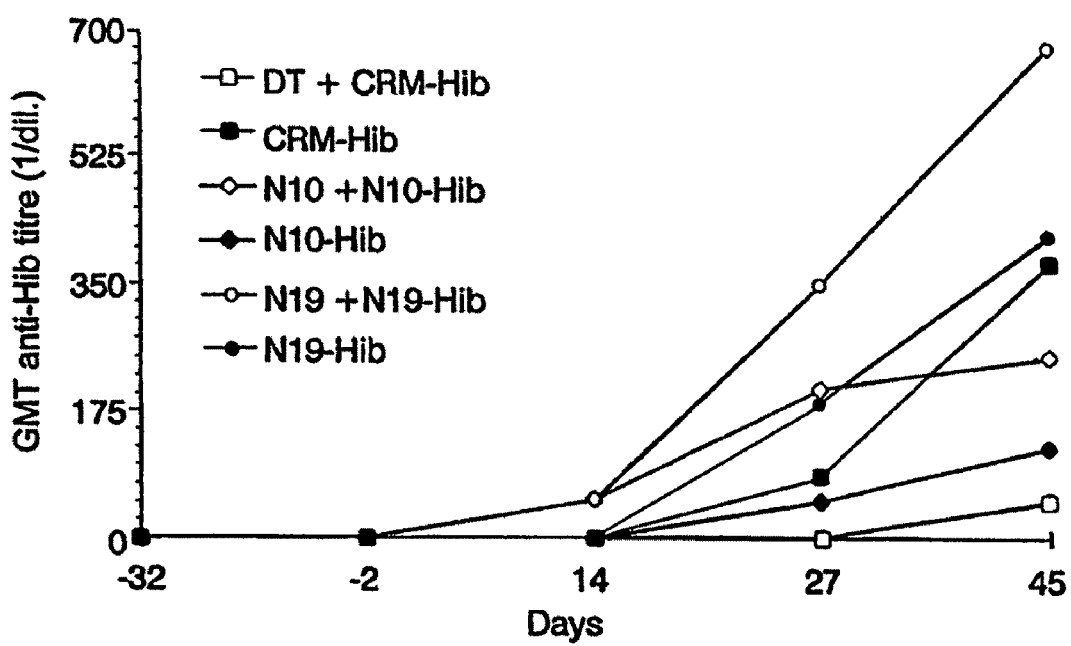
FIG. 13: Results of the immunogenicity tests performed to compare the carrier effect of N10, N19, and CRM-197, and to check for carrier induced immunosuppression phenomena. Anti-Hib titres obtained after immunising primed and unprimed CD1 mice with different conjugates.

The results are depicted in FIG. 13. In unprimed mice the best anti-Hib titres were obtained using N19-Hib, whilst CRM-Hib and N10-Hib gave lower titres. According to the known direct proportion between the size of the carrier molecules and the exerted carrier effect, N19-Hib elicited a clearly improved anti-Hib response as compared to N10-Hib. In addition N19-Hib seems slightly superior also when compared to CRM-Hib suggesting the feasibility to substitute "classical" carrier proteins with the recombinant CD4+ polyepitope proteins. In contrast to the previous immunogenicity test performed on CD1 mice, were the carrier effects of N10 and CRM-197 were similar, in this new test the mean anti-Hib titre elicited by N10-Hib was notably lower than the one obtained with CRM-Hib.

In primed mice the best results were obtained with N19-Hib, which elicited a better response also when compared to the response obtained in unprimed mice, suggesting a potentiation due to the priming with N19 protein. A slight potentiation was also obtained after priming with N10. Conversely, anti-Hib response obtained with CRM-Hib in primed mice was notably lower of the response obtained in unprimed mice, confirming the carrier induced immunosuppression often observed with the carriers in current use.

Since N10 and N19 contains five and ten tetanus toxoid T cell epitopes respectively, we subjected N10-Hib and N19-Hib to an immunogenicity test in CD1 mice primed with tetanus toxoid. The goal of this experiment was to check whether in primed mice the anti-Hib titers were improved in comparison to non-primed mice. Surprisingly, tetanus toxoid priming potentiated the immunoresponse to Hib in mice immunised with N10-Hib but not in mice that received N19-Hib (data not shown).

From the performed immunogenicity tests we can make the following few conclusions:
1. The carrier effect of the polyepitope protein is directly related to its size.
2. Recombinant polyepitope proteins N10 and N19 can parallel or exceed CRM-197 as carriers.
3. The polyepitope carrier proteins do not suffer of carrier induced suppression.

REFERENCES

Agadjanyan M, Luo P, Westerink M A J, Carey L A, Jutchins W, Steplewski Z, Weiner D B, Kieber-Emmons T (1997) Peptide mimicry of carbohydrate epitopes on human immunodeficiency virus. *Nature Biotech.* 15: 547-551.

Ahlers J. D., (1993) *J. Immunol.* 150: 5647-5665.

Anderson P, Picchichero M E, Insel R A 91985). Immunogens consisting of oligosaccharides from the capsule of *H. influenzae* type b coupled to diphtheria toxoid or the toxin protein $CRM_{197}$ *J Clin Invest* 76: 52-59.

Anderson P, Pichichero M E, Insel R A (1985). Immunization of 2-month-old infants with protein-coupled oligosaccharides derived from the capsule of *H. influenzae* type b. *J Pediatr* 107: 346-351.

Anderson P. (1983) Antibody responses to *H. Influenzae* type b and diphtheria toxin induced by conjugates of oligosaccharides of the type b capsule with the non-toxic protein CRM197. *Infect Immun.* 39: 233-238

Andreoni J, Kaythy H, Densen P (1993) Vaccination and the role of capsular polysaccharide antibody in prevention of recurrent meningococcal disease in late complement component-deficient individuals. *J. Infect. Dis.* 168: 227-231.

Bixler, G. S. et al, (1989) *Adv. Exp. Med. Biol* V:175-180.

Constantino P, Viti S, Podda A, Velmonte M. A., Nencioni L, Rappuoli R (1992). Development and phase 1 clinical testing of a conjugate vaccine against meningococcus A and C. *Vaccine* 10: 691-698.

De Velasco E A, Merkus D, Anderton S, Verheul A F M, Lizzio E F, Van der Zee R, Van Eden W, Hoffman T, Vehoef J, Snippe H (1995) Synthetic peptides representing T-cell epitopes act as carriers in pneumococcal polysaccharide conjugate vaccines. *Infect Immun* 63:961-968.

Dick W E, Beurret Mjr. Glycoconjugates of bacterial carbohydrate antigens. A survey and consideration of design and preparation factors, *Conjugate Vaccines* (J. M. Cruse and R. E. Lewis, eds.) Karger, Basel, 1989, p. 48.

Etlinger H M, Gillessen D, Lahm H W, Matile H, Schonfeld H J, Trzeciak A (1990) Use of prior vaccination for the development of new vaccines. *Science* 249: 423-425.

Goldblatt D, Levinsky R J, Turner M W (1992) Role of cell well polysaccharide in the assessment of IgG antibodies to the capsular polysaccharides of *Streptococcus pneumoniae* in childhood. *J. Infect. Dis.* 166: 632-634.

Jennings H. J. and C. Lugowsky, Immunogenic conjugates, U.S. Pat. No. 4,902,506 (1990).

Holmes S J, Granoff D M (1992) The biology of *Haemophilus influenzae* type b vaccination failure. *J. Infect. Dis.* 165: S121-S128

Insel R A, Anderson P W (1986). Oligosaccharide-protein conjugate vaccines induce and prime for oligoclonal IgG antibody responses to *H. influenzae* b capsular polysaccharide in human infants. *J Exp Med* 163: 262-269

Jennings H J, Lugowsky C (1981). Immunochemistry of group A, B, and C meningococcal polysaccharide-tetanus toxoid conjugates. *J. Immunol* 127: 1011-1018.

Kaliyaperumal A, Chauhan V S, Talwar G P Raghupathy R (1995) Carrier-induced epitope-specific regulation at its bypass in a protein-protein conjugate. *Eur J Immunol* 25: 3375-3380.

Konadu E, Schiloach G, Bryla D. A., Robins J B, Szu S C (1996) Synthesis, characterization, and immunological properties in mice of conjugates composed of detoxified lipopolysaccharides of *Salmonella paratyphi* A bound to tetanus toxoid with emphasis on the role of 0 acetyles. *Infect Immun* 64: 2709-2715.

Kumar A, Arora R, Kaur P, Chauhan V S, Sharma P (1992) "Universal" T helper cell determinants enhance immunogenicity of a *Plasmodium falciparum* merozoite surface antigen peptide. *J Immunol* 148: 1499-1505.

Lett, E. et al, (1994) *Infect Immun* 785-792.

Liptak G S, McConnochie K M, Roghmann K J, Panzer J A (1997) Decline of pediatric admissions with *Haemophilus influenzae* type b in New York state, 1982 through 1993: Relation to immunisations. *J Pediatr* 130: 923-930.

Marburg S, Jorn D, Tolman R L, Arison B, McCauley J, Kniskern P J, Hagopian A, Vella P P (1986). Bimolecular chemistry of macromolecules—synthesis of bacterial polysaccharide conjugates with *Neisseria meningitidis* membrane protein. *J. Am Chem Soc* 108, 5282.

McNamara M K, Ward R E, Kohler H (1984) Monoclonal idiotope vaccine against *Streptococcus pneumoniae* infection. *Science* 226: 1325-1326.

Moxon E R and Kroll J S (1990) The role of bacterial polysaccharide capsules as virulence factors. *Curr. Top. Microbiol. Immunol.* 150: 65-85.

Panina-Bordignon P, et al, (1989) *Eur J Immunol.* 19: 2237-2242.

Robbins J B, Schneerson R, Anderson P, Smith D H (1996) Prevention of systemic infections, especially meningitis, caused by *Haemophilus influenzae* type b: impact on public health and implications for other polysaccharide-based vaccines. *JAMA* 276: 1181-1185.

S. Marburg, R. L. Tolman, and P. J. Kniskern, Covalently-modified polyanionic bacterial polysaccharides and immunogenic protein with bigeneric spacers, and methods of preparing such polysaccharides and conjugates and of confirming covalency, U.S. Pat. Nos. 4,695,624 (1987) and 4,882,317 (1989).

Sad S, Rao K, Arora R, Talwar G P, Raghupathy R (1992) Bypass of carrier-induced epitope-specific suppression using a T-helper epitope. *Immunology* 76: 599-603.

Schneerson R, Robbins J B, Parke J C, Bell C, Schlesselman J J, Stton A, Wang Z, Schiffman G, Karpas A, Shiloach J (1986). Quantitative and qualitative analysis of serum antibodies elicited in adults by *Haemophilus influenzae* type b and pneumococcus type 6A capsular polysaccharide-tetanus toxoid conjugates. *Infect Immun* 52: 519.

Tunkel A R and Scheld W M (1993) Pathogenesis and pathophysiology of bacterial meningitis. *Clin. Microbiol. Rev.* 6:118-136.

Valmori D, Pessi A, Bianchi E, Corradin G (1992) Use of human universally antigenic tetanus toxin T cell epitopes as carriers for human vaccination. *J Immunol* 149: 717-721.

SEQUENCE LISTING

<160> NUMBER OF SEQ ID NOS: 20

<210> SEQ ID NO 1
<211> LENGTH: 15
<212> TYPE: PRT
<213> ORGANISM: T-cell epitope P23TT

<400> SEQUENCE: 1

Val Ser Ile Asp Lys Phe Arg Ile Phe Cys Lys Ala Asn Pro Lys
 1               5                  10                  15

<210> SEQ ID NO 2
<211> LENGTH: 16
<212> TYPE: PRT
<213> ORGANISM: T-cell epitope P32TT

<400> SEQUENCE: 2

Leu Lys Phe Ile Ile Lys Arg Tyr Thr Pro Asn Asn Glu Ile Asp Ser
 1               5                  10                  15

<210> SEQ ID NO 3
<211> LENGTH: 16
<212> TYPE: PRT
<213> ORGANISM: T-cell epitope P21TT

<400> SEQUENCE: 3

Ile Arg Glu Asp Asn Asn Ile Thr Leu Lys Leu Asp Arg Cys Asn Asn
 1               5                  10                  15

<210> SEQ ID NO 4
<211> LENGTH: 18
<212> TYPE: PRT
<213> ORGANISM: T-cell epitope PF T3

<400> SEQUENCE: 4

Glu Lys Lys Ile Ala Lys Met Glu Lys Ala Ser Ser Val Phe Asn Val
 1               5                  10                  15

Val Asn

<210> SEQ ID NO 5
<211> LENGTH: 21
<212> TYPE: PRT
<213> ORGANISM: T-cell epitope P30TT

<400> SEQUENCE: 5

Phe Asn Asn Phe Thr Val Ser Phe Trp Leu Arg Val Pro Lys Val Ser
 1               5                  10                  15

Ala Ser His Leu Glu
            20

<210> SEQ ID NO 6
<211> LENGTH: 14
<212> TYPE: PRT
<213> ORGANISM: T-cell epitope P2TT

<400> SEQUENCE: 6

Gln Tyr Ile Lys Ala Asn Ser Lys Phe Ile Gly Ile Thr Glu
 1               5                  10

<210> SEQ ID NO 7
<211> LENGTH: 13
<212> TYPE: PRT

-continued

```
<213> ORGANISM: T-cell epitope HA

<400> SEQUENCE: 7

Pro Lys Tyr Val Lys Gln Asn Thr Leu Lys Leu Ala Thr
  1               5                  10

<210> SEQ ID NO 8
<211> LENGTH: 20
<212> TYPE: PRT
<213> ORGANISM: T-cell epitope HBVnc

<400> SEQUENCE: 8

Pro His His Thr Ala Leu Arg Gln Ala Ile Leu Cys Trp Gly Glu Leu
  1               5                  10                  15

Met Thr Leu Ala
             20

<210> SEQ ID NO 9
<211> LENGTH: 15
<212> TYPE: PRT
<213> ORGANISM: T-cell epitope HBsAg

<400> SEQUENCE: 9

Phe Phe Leu Leu Thr Arg Ile Leu Thr Ile Pro Gln Ser Leu Asp
  1               5                  10                  15

<210> SEQ ID NO 10
<211> LENGTH: 16
<212> TYPE: PRT
<213> ORGANISM: T-cell epitope MT

<400> SEQUENCE: 10

Tyr Ser Gly Pro Leu Lys Ala Glu Ile Ala Gln Arg Leu Glu Asp Val
  1               5                  10                  15

<210> SEQ ID NO 11
<211> LENGTH: 20
<212> TYPE: PRT
<213> ORGANISM: T-cell epitope HSP70

<400> SEQUENCE: 11

Gln Pro Ser Val Gln Ile Gln Val Tyr Gln Gly Glu Arg Glu Ile Ala
  1               5                  10                  15

Ser His Asn Lys
             20

<210> SEQ ID NO 12
<211> LENGTH: 8
<212> TYPE: PRT
<213> ORGANISM: T-cell epitope Flag peptide

<400> SEQUENCE: 12

Met Asp Tyr Lys Asp Asp Asp Asp
  1               5

<210> SEQ ID NO 13
<211> LENGTH: 657
<212> TYPE: DNA
<213> ORGANISM: Recombinant N10 construct
<220> FEATURE:
<221> NAME/KEY: CDS
<222> LOCATION: (1)..(657)

<400> SEQUENCE: 13
```

-continued

```
atg ggg ggt tct cat cat cat cat cat ggt atg gct agc atg gat        48
Met Gly Gly Ser His His His His His Gly Met Ala Ser Met Asp
 1               5                  10                  15 tac aag gac gac gat gat atc gaa ggt cgc aaa ggt gtt tcc atc gac    96
Tyr Lys Asp Asp Asp Asp Ile Glu Gly Arg Lys Gly Val Ser Ile Asp
                 20                  25                  30 aaa ttc cgt atc ttc tgc aaa gct aac ccg aaa aaa ggt ctg aaa ttc   144
Lys Phe Arg Ile Phe Cys Lys Ala Asn Pro Lys Lys Gly Leu Lys Phe
             35                  40                  45 atc atc aaa cgt tac acc ccg aac aac gaa atc gac tcc aaa ggt atc   192
Ile Ile Lys Arg Tyr Thr Pro Asn Asn Glu Ile Asp Ser Lys Gly Ile
         50                  55                  60 cgt gaa gac aac aac atc acc ctg aaa ctg gac cgt tgc aac aac aaa   240
Arg Glu Asp Asn Asn Ile Thr Leu Lys Leu Asp Arg Cys Asn Asn Lys
 65                  70                  75                  80 ggt gaa aag aag atc gct aaa atg gaa aaa gct tct tct gtt ttc aac   288
Gly Glu Lys Lys Ile Ala Lys Met Glu Lys Ala Ser Ser Val Phe Asn
                 85                  90                  95 gtt gtt aac tct aaa ggt ttc aac aac ttc acc gtt tcc ttc tgg ctg   336
Val Val Asn Ser Lys Gly Phe Asn Asn Phe Thr Val Ser Phe Trp Leu
            100                 105                 110 cgt gtt ccg aaa gtt tcc gct tcc cac ctg gaa aaa ggt cag tac atc   384
Arg Val Pro Lys Val Ser Ala Ser His Leu Glu Lys Gly Gln Tyr Ile
        115                 120                 125 aaa gct aac tcc aaa ttc atc ggt atc acc gaa aaa ggt gga tct ccg   432
Lys Ala Asn Ser Lys Phe Ile Gly Ile Thr Glu Lys Gly Gly Ser Pro
    130                 135                 140 cat cat acc gcg ctg cgc cag gcg att ctg tgc tgg ggc gaa ctg atg   480
His His Thr Ala Leu Arg Gln Ala Ile Leu Cys Trp Gly Glu Leu Met
145                 150                 155                 160 acc ctg gcg aaa gga tct ccg aaa tat gtg aaa cag aac acc ctg aaa   528
Thr Leu Ala Lys Gly Ser Pro Lys Tyr Val Lys Gln Asn Thr Leu Lys
                165                 170                 175 ctg gcg acc aaa gga tcg ttt ttt ctg ctg acc cgc att ctg acc att   576
Leu Ala Thr Lys Gly Ser Phe Phe Leu Leu Thr Arg Ile Leu Thr Ile
            180                 185                 190 ccg cag tct ctg gat aaa ggc tat tct ggc ccg ctg aaa gcg gaa att   624
Pro Gln Ser Leu Asp Lys Gly Tyr Ser Gly Pro Leu Lys Ala Glu Ile
        195                 200                 205 gcg cag cgc ctg gaa gat gtg aaa gga tcc taa                       657
Ala Gln Arg Leu Glu Asp Val Lys Gly Ser
    210                 215
```

<210> SEQ ID NO 14
<211> LENGTH: 218
<212> TYPE: PRT
<213> ORGANISM: Recombinant N10 construct

<400> SEQUENCE: 14

Met Gly Gly Ser His His His His His Gly Met Ala Ser Met Asp
 1               5                  10                  15

Tyr Lys Asp Asp Asp Asp Ile Glu Gly Arg Lys Gly Val Ser Ile Asp
                 20                  25                  30

Lys Phe Arg Ile Phe Cys Lys Ala Asn Pro Lys Lys Gly Leu Lys Phe
             35                  40                  45

Ile Ile Lys Arg Tyr Thr Pro Asn Asn Glu Ile Asp Ser Lys Gly Ile
         50                  55                  60

Arg Glu Asp Asn Asn Ile Thr Leu Lys Leu Asp Arg Cys Asn Asn Lys
 65                  70                  75                  80

```
Gly Glu Lys Lys Ile Ala Lys Met Glu Lys Ala Ser Ser Val Phe Asn
                85                  90                  95

Val Val Asn Ser Lys Gly Phe Asn Asn Phe Thr Val Ser Phe Trp Leu
            100                 105                 110

Arg Val Pro Lys Val Ser Ala Ser His Leu Glu Lys Gly Gln Tyr Ile
        115                 120                 125

Lys Ala Asn Ser Lys Phe Ile Gly Ile Thr Glu Lys Gly Gly Ser Pro
    130                 135                 140

His His Thr Ala Leu Arg Gln Ala Ile Leu Cys Trp Gly Glu Leu Met
145                 150                 155                 160

Thr Leu Ala Lys Gly Ser Pro Lys Tyr Val Lys Gln Asn Thr Leu Lys
                165                 170                 175

Leu Ala Thr Lys Gly Ser Phe Phe Leu Leu Thr Arg Ile Leu Thr Ile
            180                 185                 190

Pro Gln Ser Leu Asp Lys Gly Tyr Ser Gly Pro Leu Lys Ala Glu Ile
        195                 200                 205

Ala Gln Arg Leu Glu Asp Val Lys Gly Ser
    210                 215
```

```
<210> SEQ ID NO 15
<211> LENGTH: 432
<212> TYPE: DNA
<213> ORGANISM: Recombinant N6 construct
<220> FEATURE:
<221> NAME/KEY: CDS
<222> LOCATION: (1)..(432)

<400> SEQUENCE: 15
```

```
atg ggg ggt tct cat cat cat cat cat cat ggt atg gct agc atg gat        48
Met Gly Gly Ser His His His His His His Gly Met Ala Ser Met Asp
  1               5                  10                  15 tac aag gac gac gat gat atc gaa ggt cgc aaa ggt gtt tcc atc gac        96
Tyr Lys Asp Asp Asp Asp Ile Glu Gly Arg Lys Gly Val Ser Ile Asp
             20                  25                  30 aaa ttc cgt atc ttc tgc aaa gct aac ccg aaa aaa ggt ctg aaa ttc       144
Lys Phe Arg Ile Phe Cys Lys Ala Asn Pro Lys Lys Gly Leu Lys Phe
         35                  40                  45 atc atc aaa cgt tac acc ccg aac aac gaa atc gac tcc aaa ggt atc       192
Ile Ile Lys Arg Tyr Thr Pro Asn Asn Glu Ile Asp Ser Lys Gly Ile
     50                  55                  60 cgt gaa gac aac aac atc acc ctg aaa ctg gac cgt tgc aac aac aaa       240
Arg Glu Asp Asn Asn Ile Thr Leu Lys Leu Asp Arg Cys Asn Asn Lys
 65                  70                  75                  80 ggt gaa aag aag atc gct aaa atg gaa aaa gct tct tct gtt ttc aac       288
Gly Glu Lys Lys Ile Ala Lys Met Glu Lys Ala Ser Ser Val Phe Asn
                 85                  90                  95 gtt gtt aac tct aaa ggt ttc aac aac ttc acc gtt tcc ttc tgg ctg       336
Val Val Asn Ser Lys Gly Phe Asn Asn Phe Thr Val Ser Phe Trp Leu
            100                 105                 110 cgt gtt ccg aaa gtt tcc gct tcc cac ctg gaa aaa ggt cag tac atc       384
Arg Val Pro Lys Val Ser Ala Ser His Leu Glu Lys Gly Gln Tyr Ile
        115                 120                 125 aaa gct aac tcc aaa ttc atc ggt atc acc gaa aaa ggt gga tcc taa       432
Lys Ala Asn Ser Lys Phe Ile Gly Ile Thr Glu Lys Gly Gly Ser
    130                 135                 140
```

```
<210> SEQ ID NO 16
<211> LENGTH: 143
<212> TYPE: PRT
<213> ORGANISM: Recombinant N6 construct
```

<400> SEQUENCE: 16

```
Met Gly Gly Ser His His His His His Gly Met Ala Ser Met Asp
 1               5                  10                  15

Tyr Lys Asp Asp Asp Asp Ile Glu Gly Arg Lys Gly Val Ser Ile Asp
             20                  25                  30

Lys Phe Arg Ile Phe Cys Lys Ala Asn Pro Lys Lys Gly Leu Lys Phe
         35                  40                  45

Ile Ile Lys Arg Tyr Thr Pro Asn Asn Glu Ile Asp Ser Lys Gly Ile
 50                  55                  60

Arg Glu Asp Asn Asn Ile Thr Leu Lys Leu Asp Arg Cys Asn Asn Lys
 65                  70                  75                  80

Gly Glu Lys Lys Ile Ala Lys Met Glu Lys Ala Ser Ser Val Phe Asn
             85                  90                  95

Val Val Asn Ser Lys Gly Phe Asn Asn Phe Thr Val Ser Phe Trp Leu
            100                 105                 110

Arg Val Pro Lys Val Ser Ala Ser His Leu Glu Lys Gly Gln Tyr Ile
        115                 120                 125

Lys Ala Asn Ser Lys Phe Ile Gly Ile Thr Glu Lys Gly Gly Ser
        130                 135                 140
```

<210> SEQ ID NO 17
<211> LENGTH: 1173
<212> TYPE: DNA
<213> ORGANISM: Recombinant N19 construct
<220> FEATURE:
<221> NAME/KEY: CDS
<222> LOCATION: (1)..(1173)

<400> SEQUENCE: 17

```
atg ggg ggt tct cat cat cat cat cat cat ggt atg gct agc atg gat      48
Met Gly Gly Ser His His His His His His Gly Met Ala Ser Met Asp
 1               5                  10                  15 tac aag gac gac gat gat atc gaa ggt cgc aaa ggt gtt tcc atc gac      96
Tyr Lys Asp Asp Asp Asp Ile Glu Gly Arg Lys Gly Val Ser Ile Asp
             20                  25                  30 aaa ttc cgt atc ttc tgc aaa gct aac ccg aaa aaa ggt ctg aaa ttc     144
Lys Phe Arg Ile Phe Cys Lys Ala Asn Pro Lys Lys Gly Leu Lys Phe
         35                  40                  45 atc atc aaa cgt tac acc ccg aac aac gaa atc gac tcc aaa ggt atc     192
Ile Ile Lys Arg Tyr Thr Pro Asn Asn Glu Ile Asp Ser Lys Gly Ile
 50                  55                  60 cgt gaa gac aac aac atc acc ctg aaa ctg gac cgt tgc aac aac aaa     240
Arg Glu Asp Asn Asn Ile Thr Leu Lys Leu Asp Arg Cys Asn Asn Lys
 65                  70                  75                  80 ggt gaa aag aag atc gct aaa atg gaa aaa gct tct tct gtt ttc aac     288
Gly Glu Lys Lys Ile Ala Lys Met Glu Lys Ala Ser Ser Val Phe Asn
             85                  90                  95 gtt gtt aac tct aaa ggt ttc aac aac ttc acc gtt tcc ttc tgg ctg     336
Val Val Asn Ser Lys Gly Phe Asn Asn Phe Thr Val Ser Phe Trp Leu
            100                 105                 110 cgt gtt ccg aaa gtt tcc gct tcc cac ctg gaa aaa ggt cag tac atc     384
Arg Val Pro Lys Val Ser Ala Ser His Leu Glu Lys Gly Gln Tyr Ile
        115                 120                 125 aaa gct aac tcc aaa ttc atc ggt atc acc gaa aaa ggt gga tct ccg     432
Lys Ala Asn Ser Lys Phe Ile Gly Ile Thr Glu Lys Gly Gly Ser Pro
        130                 135                 140 cat cat acc gcg ctg cgc cag gcg att ctg tgc tgg ggc gaa ctg atg     480
His His Thr Ala Leu Arg Gln Ala Ile Leu Cys Trp Gly Glu Leu Met
```

-continued

```
                145                 150                 155                 160
acc ctg gcg aaa gga tct ccg aaa tat gtg aaa cag aac acc ctg aaa         528
Thr Leu Ala Lys Gly Ser Pro Lys Tyr Val Lys Gln Asn Thr Leu Lys
                165                 170                 175 ctg gcg acc aaa gga tcg ttt ttt ctg ctg acc cgc att ctg acc att         576
Leu Ala Thr Lys Gly Ser Phe Phe Leu Leu Thr Arg Ile Leu Thr Ile
            180                 185                 190 ccg cag tct ctg gat aaa ggc tat tct ggc ccg ctg aaa gcg gaa att         624
Pro Gln Ser Leu Asp Lys Gly Tyr Ser Gly Pro Leu Lys Ala Glu Ile
        195                 200                 205 gcg cag cgc ctg gaa gat gtg aaa gga tct gtt tcc atc gac aaa ttc         672
Ala Gln Arg Leu Glu Asp Val Lys Gly Ser Val Ser Ile Asp Lys Phe
    210                 215                 220 cgt atc ttc tgc aaa gct aac ccg aaa aaa ggt ctg aaa ttc atc atc         720
Arg Ile Phe Cys Lys Ala Asn Pro Lys Lys Gly Leu Lys Phe Ile Ile
225                 230                 235                 240 aaa cgt tac acc ccg aac aac gaa atc gac tcc aaa ggt atc cgt gaa         768
Lys Arg Tyr Thr Pro Asn Asn Glu Ile Asp Ser Lys Gly Ile Arg Glu
                245                 250                 255 gac aac aac atc acc ctg aaa ctg gac cgt tgc aac aac aaa ggt gaa         816
Asp Asn Asn Ile Thr Leu Lys Leu Asp Arg Cys Asn Asn Lys Gly Glu
            260                 265                 270 aag aag atc gct aaa atg gaa aaa gct tct tct gtt ttc aac gtt gtt         864
Lys Lys Ile Ala Lys Met Glu Lys Ala Ser Ser Val Phe Asn Val Val
        275                 280                 285 aac tct aaa ggt ttc aac aac ttc acc gtt tcc ttc tgg ctg cgt gtt         912
Asn Ser Lys Gly Phe Asn Asn Phe Thr Val Ser Phe Trp Leu Arg Val
    290                 295                 300 ccg aaa gtt tcc gct tcc cac ctg gaa aaa ggt cag tac atc aaa gct         960
Pro Lys Val Ser Ala Ser His Leu Glu Lys Gly Gln Tyr Ile Lys Ala
305                 310                 315                 320 aac tcc aaa ttc atc ggt atc acc gaa aaa ggt gga tct ccg cat cat        1008
Asn Ser Lys Phe Ile Gly Ile Thr Glu Lys Gly Gly Ser Pro His His
                325                 330                 335 acc gcg ctg cgc cag gcg att ctg tgc tgg ggc gaa ctg atg acc ctg        1056
Thr Ala Leu Arg Gln Ala Ile Leu Cys Trp Gly Glu Leu Met Thr Leu
            340                 345                 350 gcg aaa gga tct ccg aaa tat gtg aaa cag aac acc ctg aaa ctg gcg        1104
Ala Lys Gly Ser Pro Lys Tyr Val Lys Gln Asn Thr Leu Lys Leu Ala
        355                 360                 365 acc aaa gga tcg ttt ttt ctg ctg acc cgc att ctg acc att ccg cag        1152
Thr Lys Gly Ser Phe Phe Leu Leu Thr Arg Ile Leu Thr Ile Pro Gln
    370                 375                 380 tct ctg gat aaa gga tcc taa                                             1173
Ser Leu Asp Lys Gly Ser
385                 390

<210> SEQ ID NO 18
<211> LENGTH: 390
<212> TYPE: PRT
<213> ORGANISM: Recombinant N19 construct

<400> SEQUENCE: 18

Met Gly Gly Ser His His His His His His Gly Met Ala Ser Met Asp
1               5                   10                  15

Tyr Lys Asp Asp Asp Asp Ile Glu Gly Arg Lys Gly Val Ser Ile Asp
                20                  25                  30

Lys Phe Arg Ile Phe Cys Lys Ala Asn Pro Lys Lys Gly Leu Lys Phe
            35                  40                  45
```

```
Ile Ile Lys Arg Tyr Thr Pro Asn Asn Glu Ile Asp Ser Lys Gly Ile
 50                  55                  60

Arg Glu Asp Asn Asn Ile Thr Leu Lys Leu Asp Arg Cys Asn Asn Lys
 65                  70                  75                  80

Gly Glu Lys Lys Ile Ala Lys Met Glu Lys Ala Ser Ser Val Phe Asn
                 85                  90                  95

Val Val Asn Ser Lys Gly Phe Asn Asn Phe Thr Val Ser Phe Trp Leu
            100                 105                 110

Arg Val Pro Lys Val Ser Ala Ser His Leu Glu Lys Gly Gln Tyr Ile
            115                 120                 125

Lys Ala Asn Ser Lys Phe Ile Gly Ile Thr Glu Lys Gly Gly Ser Pro
            130                 135                 140

His His Thr Ala Leu Arg Gln Ala Ile Leu Cys Trp Gly Glu Leu Met
145                 150                 155                 160

Thr Leu Ala Lys Gly Ser Pro Lys Tyr Val Lys Gln Asn Thr Leu Lys
                165                 170                 175

Leu Ala Thr Lys Gly Ser Phe Phe Leu Leu Thr Arg Ile Leu Thr Ile
            180                 185                 190

Pro Gln Ser Leu Asp Lys Gly Tyr Ser Gly Pro Leu Lys Ala Glu Ile
            195                 200                 205

Ala Gln Arg Leu Glu Asp Val Lys Gly Ser Val Ser Ile Asp Lys Phe
            210                 215                 220

Arg Ile Phe Cys Lys Ala Asn Pro Lys Lys Gly Leu Lys Phe Ile Ile
225                 230                 235                 240

Lys Arg Tyr Thr Pro Asn Asn Glu Ile Asp Ser Lys Gly Ile Arg Glu
                245                 250                 255

Asp Asn Asn Ile Thr Leu Lys Leu Asp Arg Cys Asn Asn Lys Gly Glu
            260                 265                 270

Lys Lys Ile Ala Lys Met Glu Lys Ala Ser Ser Val Phe Asn Val Val
            275                 280                 285

Asn Ser Lys Gly Phe Asn Asn Phe Thr Val Ser Phe Trp Leu Arg Val
            290                 295                 300

Pro Lys Val Ser Ala Ser His Leu Glu Lys Gly Gln Tyr Ile Lys Ala
305                 310                 315                 320

Asn Ser Lys Phe Ile Gly Ile Thr Glu Lys Gly Gly Ser Pro His His
                325                 330                 335

Thr Ala Leu Arg Gln Ala Ile Leu Cys Trp Gly Glu Leu Met Thr Leu
            340                 345                 350

Ala Lys Gly Ser Pro Lys Tyr Val Lys Gln Asn Thr Leu Lys Leu Ala
            355                 360                 365

Thr Lys Gly Ser Phe Phe Leu Leu Thr Arg Ile Leu Thr Ile Pro Gln
            370                 375                 380

Ser Leu Asp Lys Gly Ser
385                 390

<210> SEQ ID NO 19
<211> LENGTH: 723
<212> TYPE: DNA
<213> ORGANISM: Recombinant N11 construct
<220> FEATURE:
<221> NAME/KEY: CDS
<222> LOCATION: (1)..(723)

<400> SEQUENCE: 19 atg ggg ggt tct cat cat cat cat cat cat ggt atg gct agc atg gat      48
Met Gly Gly Ser His His His His His His Gly Met Ala Ser Met Asp
```

```
                1               5               10              15
tac aag gac gac gat gat atc gaa ggt cgc aaa ggt gtt tcc atc gac      96
Tyr Lys Asp Asp Asp Asp Ile Glu Gly Arg Lys Gly Val Ser Ile Asp
                    20              25              30 aaa ttc cgt atc ttc tgc aaa gct aac ccg aaa aaa ggt ctg aaa ttc     144
Lys Phe Arg Ile Phe Cys Lys Ala Asn Pro Lys Lys Gly Leu Lys Phe
            35              40              45 atc atc aaa cgt tac acc ccg aac aac gaa atc gac tcc aaa ggt atc     192
Ile Ile Lys Arg Tyr Thr Pro Asn Asn Glu Ile Asp Ser Lys Gly Ile
        50              55              60 cgt gaa gac aac aac atc acc ctg aaa ctg gac cgt tgc aac aac aaa     240
Arg Glu Asp Asn Asn Ile Thr Leu Lys Leu Asp Arg Cys Asn Asn Lys
65              70              75              80 ggt gaa aag aag atc gct aaa atg gaa aaa gct tct tct gtt ttc aac     288
Gly Glu Lys Lys Ile Ala Lys Met Glu Lys Ala Ser Ser Val Phe Asn
                85              90              95 gtt gtt aac tct aaa ggt ttc aac aac ttc acc gtt tcc ttc tgg ctg     336
Val Val Asn Ser Lys Gly Phe Asn Asn Phe Thr Val Ser Phe Trp Leu
            100             105             110 cgt gtt ccg aaa gtt tcc gct tcc cac ctg gaa aaa ggt cag tac atc     384
Arg Val Pro Lys Val Ser Ala Ser His Leu Glu Lys Gly Gln Tyr Ile
        115             120             125 aaa gct aac tcc aaa ttc atc ggt atc acc gaa aaa ggt gga tct ccg     432
Lys Ala Asn Ser Lys Phe Ile Gly Ile Thr Glu Lys Gly Gly Ser Pro
130             135             140 cat cat acc gcg ctg cgc cag gcg att ctg tgc tgg ggc gaa ctg atg     480
His His Thr Ala Leu Arg Gln Ala Ile Leu Cys Trp Gly Glu Leu Met
145             150             155             160 acc ctg gcg aaa gga tct ccg aaa tat gtg aaa cag aac acc ctg aaa     528
Thr Leu Ala Lys Gly Ser Pro Lys Tyr Val Lys Gln Asn Thr Leu Lys
                165             170             175 ctg gcg acc aaa gga tcg ttt ttt ctg ctg acc cgc att ctg acc att     576
Leu Ala Thr Lys Gly Ser Phe Phe Leu Leu Thr Arg Ile Leu Thr Ile
            180             185             190 ccg cag tct ctg gat aaa ggc tat tct ggc ccg ctg aaa gcg gaa att     624
Pro Gln Ser Leu Asp Lys Gly Tyr Ser Gly Pro Leu Lys Ala Glu Ile
        195             200             205 gcg cag cgc ctg gaa gat gtg aaa gga tct cag ccg tct gtt cag att     672
Ala Gln Arg Leu Glu Asp Val Lys Gly Ser Gln Pro Ser Val Gln Ile
210             215             220 cag gtg tat cag ggt gaa cgt gaa atc gca tct cat aac aaa gga tcc     720
Gln Val Tyr Gln Gly Glu Arg Glu Ile Ala Ser His Asn Lys Gly Ser
225             230             235             240 taa                                                                 723
```

<210> SEQ ID NO 20
<211> LENGTH: 240
<212> TYPE: PRT
<213> ORGANISM: Recombinant N11 construct

<400> SEQUENCE: 20

Met Gly Gly Ser His His His His His Gly Met Ala Ser Met Asp
1               5                   10                  15

Tyr Lys Asp Asp Asp Asp Ile Glu Gly Arg Lys Gly Val Ser Ile Asp
                    20              25              30

Lys Phe Arg Ile Phe Cys Lys Ala Asn Pro Lys Lys Gly Leu Lys Phe
            35              40              45

Ile Ile Lys Arg Tyr Thr Pro Asn Asn Glu Ile Asp Ser Lys Gly Ile
        50              55              60

-continued

```
Arg Glu Asp Asn Asn Ile Thr Leu Lys Leu Asp Arg Cys Asn Asn Lys
 65                  70                  75                  80

Gly Glu Lys Lys Ile Ala Lys Met Glu Lys Ala Ser Ser Val Phe Asn
             85                   90                  95

Val Val Asn Ser Lys Gly Phe Asn Asn Phe Thr Val Ser Phe Trp Leu
            100                 105             110

Arg Val Pro Lys Val Ser Ala Ser His Leu Glu Lys Gly Gln Tyr Ile
        115                 120             125

Lys Ala Asn Ser Lys Phe Ile Gly Ile Thr Glu Lys Gly Gly Ser Pro
        130                 135             140

His His Thr Ala Leu Arg Gln Ala Ile Leu Cys Trp Gly Glu Leu Met
145                 150                 155                 160

Thr Leu Ala Lys Gly Ser Pro Lys Tyr Val Lys Gln Asn Thr Leu Lys
            165                 170                 175

Leu Ala Thr Lys Gly Ser Phe Phe Leu Leu Thr Arg Ile Leu Thr Ile
            180                 185                 190

Pro Gln Ser Leu Asp Lys Gly Tyr Ser Gly Pro Leu Lys Ala Glu Ile
        195                 200                 205

Ala Gln Arg Leu Glu Asp Val Lys Gly Ser Gln Pro Ser Val Gln Ile
        210                 215                 220

Gln Val Tyr Gln Gly Glu Arg Glu Ile Ala Ser His Asn Lys Gly Ser
225                 230                 235                 240
```

The invention claimed is:

1. A carrier protein comprising at least five different CD4+ T cell epitopes, wherein the CD4+ T cell epitopes are CD4+ T cell epitopes from tetanus toxin, *Plasmodium falciparum* circumsporozite protein, hepatitis B surface antigen, hepatitis B nuclear core protein, influenza matrix protein, influenza haemagglutinin, diphtheria toxoid, diphtheria toxin mutant CRM197, group B *Neisseria meningitidis* outer membrane protein complex, pertussis toxin or heat shock protein 70, wherein said carrier protein lacks B-cell and T-suppressor epitopes.

2. The carrier protein of claim 1, wherein the CD4+ T cell epitopes are selected from P23TT, P32TT, P21TT, PFT3, P30TT, P2TT, HBVnc, influenza haemagglutinin (HA), HbsAg, influenza matrix (MT) and hsp70 CD4+ T-cell epitopes.

3. The carrier protein of claim 1, wherein the carrier protein comprises P23TT, P32TT, P21TT, PFT3, P30TT, P2TT, HBVnc, influenza haemagglutinin (HA), HbsAg, and influenza matrix (MT) CD4+ T-cell epitopes.

4. The carrier protein of claim 1, wherein the carrier protein comprises P23TT, P32TT, P21TT, PFT3, P30TT, P2TT, HBVnc, influenza haemagglutinin (HA), HbsAg, influenza matrix (MT) and hsp70 CD4+ T-cell epitopes.

5. The carrier protein of claim 1, wherein the carrier protein comprises P23TT, P32TT, P21TT, PFT3, P30TT, and P2TT CD4+ T-cell epitopes.

6. The carrier protein of claim 1, wherein the CD4+ T cell epitopes are human CD4+ T-cell epitopes.

7. The carrier protein of claim 1, wherein the carrier protein comprises one or more of the N6, N10 or N19 proteins.

8. The carrier protein of claim 1, wherein the carrier protein comprises P23TT, P32TT, P21TT, PFT3, P30TT, P2TT, HBVnc, influenza haemagglutinin (HA), and HbsAg CD4+ T cell epitopes.

* * * * *